(12) United States Patent
Tsai et al.

(10) Patent No.: US 11,242,516 B2
(45) Date of Patent: Feb. 8, 2022

(54) METHOD FOR EX VIVO TREATING BLOOD OR PLASMA

(71) Applicant: INDUSTRIAL TECHNOLOGY RESEARCH INSTITUTE, Hsinchu (TW)

(72) Inventors: Pei-Yi Tsai, Hsinchu (TW); Chih-Hung Chen, Tainan (TW); Yi-Hung Lin, Zhubei (TW); Chih-Chieh Huang, Zhunan Township (TW); Hsin-Hsin Shen, Zhudong Township (TW); Liang-Yin Ke, Kaohsiung (TW); Chu-Huang Chen, Taichung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 463 days.

(21) Appl. No.: 16/137,925

(22) Filed: Sep. 21, 2018

(65) Prior Publication Data
US 2019/0010483 A1    Jan. 10, 2019

Related U.S. Application Data

(62) Division of application No. 14/984,938, filed on Dec. 30, 2015, now abandoned.

(30) Foreign Application Priority Data

Aug. 11, 2015 (TW) .................................. 104126050
Nov. 23, 2015 (CN) ......................... 201510815421.4

(51) Int. Cl.
| | |
|---|---|
| *C12N 11/12* | (2006.01) |
| *A61M 1/34* | (2006.01) |
| *C12N 11/14* | (2006.01) |
| *C12M 1/00* | (2006.01) |
| *C12N 11/10* | (2006.01) |

(52) U.S. Cl.
CPC ........... *C12N 11/12* (2013.01); *A61M 1/3486* (2014.02); *C12M 45/09* (2013.01); *C12N 11/10* (2013.01); *C12N 11/14* (2013.01); *A61M 2202/08* (2013.01)

(58) Field of Classification Search
CPC ....... C12N 11/12; C12N 9/2402; C12M 45/09
See application file for complete search history.

(56) References Cited

U.S. PATENT DOCUMENTS

| | | |
|---|---|---|
| 4,331,767 A | 5/1982 | Nakajima et al. |
| 5,118,613 A | 6/1992 | McGowan |
| 5,232,696 A | 8/1993 | Lees et al. |
| 5,998,183 A | 12/1999 | Le Fevre et al. |
| 7,781,408 B2 | 8/2010 | Clandinin et al. |
| 7,914,781 B2 | 3/2011 | Higuchi |
| 7,968,529 B2 | 6/2011 | Nieuwenhuizen |
| 8,551,940 B2 | 10/2013 | de Lourdes Higuchi |
| 2007/0074300 A1 | 3/2007 | Igdoura et al. |
| 2010/0087363 A1 | 4/2010 | Rubinstein et al. |
| 2010/0190146 A1 | 7/2010 | Rynum et al. |
| 2011/0182875 A1* | 7/2011 | Fang ................... C07K 14/475 424/94.61 |

FOREIGN PATENT DOCUMENTS

| | | |
|---|---|---|
| CN | 101370536 A | 2/2009 |
| CN | 102091595 A | 6/2011 |
| TW | 201306865 A1 | 2/2013 |

OTHER PUBLICATIONS

Miyagi ("Mammalian sialidases: Physiological and pathological roles in cellular functions" Glycobiology, vol. 22 No. 7, 2012, 880-896). (Year: 2012).*
Of Costa ("Enyme Immobilization in Biodegradable Polymers for Biomedical Applications", Chapter 17, Biodegradable Systems in Tissue Engineering and Regenerative Medicine, 2004, CRC Press, First Edition, Boca Raton Florida, pp. 301-323 (Year: 2004).*
Aviram M., "Plasma Lipoprotein Separation by Discontinuous Density Gradient Ultracentrifugation in Hyperlipoproteinemic Patients", Biochem. Med., 30, 1983, p. 111-118.
Avogaro P, et al., "Presence of a Modified Low Density Lipoprotein in Humans", Arteriosclerosis, vol. 8, No. 1, 1988, p. 79-87.

(Continued)

*Primary Examiner* — Robert J Yamasaki
*Assistant Examiner* — Charles Zoltan Constantine
(74) *Attorney, Agent, or Firm* — Birch, Stewart, Kolasch & Birch, LLP

(57) ABSTRACT

A method for ex vivo treating blood or plasma is provided. The method includes (a) ex vivo contacting a blood or plasma with an enzyme composition to react the enzyme composition with the blood or plasma, wherein the enzyme composition is capable of eliminating electronegative low-density lipoprotein from the blood or plasma by the activity of the enzyme composition, and the enzyme composition is selected from a group consisting of: a first enzyme for eliminating a glycan residue of an electronegative low-density lipoprotein (LDL); a second enzyme for eliminating ceramide carried by a electronegative low-density lipoprotein (LDL); and a combination thereof; and (b) terminating contact between the blood or plasma and the enzyme composition to terminate the reaction of the enzyme composition with the blood or plasma.

18 Claims, 26 Drawing Sheets
Specification includes a Sequence Listing.

(56) References Cited

OTHER PUBLICATIONS

Casals-Stenzel J, et al., "Pharmacological Actions of Web 2086, a New Specific Antagonist of Platelet Activating Factor", The Journal of Pharmacology and Experimental Therapeutics, 1987, p. 974-981.
Chen CH, et al., "Low-Density Lipoprotein in Hypercholesterolemic Human Plasma Induces Vascular Endothelial Cell Apoptosis by Inhibiting Fibroblast Growth Factor 2 Transcription", Circulation, 2003, p. 2102-2108.
Estruch et al., "Electronegative LDL: A Circulating Modified LDL with a Role in Inflammation," Mediators of Inflammation, vol. 2013, Article ID 181324, 2013, 14 pages.
Geromanos SJ, et al., "The detection, correlation, and comparison of peptide precursor and product ions from data independent LC-MS with data dependant LC-MS/MS", Proteomics, 9, 2009, p. 1683-1695.
Hoff HF, et al., "Correlation in the human aorta of apo B fractions with tissue cholesterol and collagen content", Atherosclerosis, 32, (1979), p. 259-268.
Hoff HF, et al., "Isolation, Purification, and Characterization of a Lipoprotein Containing Apo B from the Human Aorta", Atherosclerosis, 42, 1982, p. 273-297.
KE et al., "The Underlying Chemistry of Electronegative LDL's Atherogenicity," Current Atherosclerosis Reports, vol. 16, No. 428, 2014 (published online Jun. 3, 2014), 12 pages.
Li GZ, et al., "Database searching and accounting of multiplexed precursor and product ion spectra from the data independent analysis of simple and complex peptide mixtures", Proteomics, 9, 2009, p. 1696-1719.
Of Tringali, "Properties of Recombinant Human Cytosolic Sialidase HsNeu2", The Journal of Biological Chemistry, 2004, vol. 279, Issue 5, Jan. 2004 3169-3179 (Year:2004).
Orekhov et al., "Modified Low Density Lipoprotein and Lipoprotein-Containing Circulating Immune Complexes as Diagnostic and Prognostic Biomarkers of Atherosclerosis and Type 1 Diabetes Macrovascular Disease," International Journal of Molecular Sciences, vol. 15, 2014, pp. 12807-12841.
Sakamoto N, et al., "Role of LOX-1 in Monocyte Adhesion-Triggered Redox, Akt/eNOS and Ca2+ Signaling Pathways in Endothelial Cells", Journal of Cellular Physiology, 2009, p. 706-715.
Silva JC, et al., "Absolute Quantification of Proteins by LCMSe: A virtue of parallel MS acquisition", Mol. Cell. Proteomics, 2006, p. 144-156.
Silva JC, et al., "Quantitative Proteomic Analysis by Accurate Mass Retention Time Pairs", Anal. Chem., 2005, 77, p. 2187-2200.
Taiwanese Office Action and Search Report, dated Aug. 25, 2016, for Taiwanese Application No. 104126050.
Tang D, et al., "Electronegative LDL circulating in smokers impairs endothelial progenitor cell differentiation by inhibiting Akt phosphorylation via LOX-1", J. Lipid. Res., 49, 2008, p. 33-47.
Yang CY, et al., "Isolation, Characterization, and Functional Assessment of Oxidatively Modified Subfractions of Circulating Low-Density Lipoproteins", Arterioscler Thromb Vase Bioi., 2003, p. 1083-1090.
Yang CY, et al., "Pro-apoptotic low-density lipoprotein subtractions in type II diabetes", Atherosclerosis, 2007, p. 283-291.
Chinese Office Action and Search Report for Chinese Application No. 201510815421.4, dated Aug. 29, 2018.
Gang et al., "Correlation research between serum sialic acid and Coronary heart disease as well as its risk factors", Medical Laboratory Science and Clinics, vol. 19, No. 3, pp. 43-44, 2008, with English abstract.
Houlijuan et al., "Glycosylated Low Density Lipoprotein and Atherosclerosis", Journal of North China Coal Medical College, vol. 4, No. 5, pp. 575-576, Dec. 31, 2002, with partial English translation.
Ren et al., "Ceramide and Metabolic Syndrome", International Journal of Endocrinology and Metabolism, vol. 27, No. 1, pp. 16-18, Jan. 31, 2007, with English abstract.
Zhang et al., "Advance of the Studies on Low-Density Lipoprotein Apheresis", Pharmaceutical Biotechnology, vol. 11, No. 2, pp. 116-120, Jun. 25, 2004, with English abstract.

* cited by examiner

| Start | End | Rt | sequence/ intensity | buffer control | A-01(1) | A-01(3) | CD-01 | SiNu 0.5 | SiNu 1 | |
|---|---|---|---|---|---|---|---|---|---|---|
| 1647 | 1661 | 21.0709 | (R)IGQDGISTSATTNLK(C) (SEQ ID NO.3) | 299379 | 258251 | - | 499202 | 254127 | - | apo B100 |
| | | 28.1737 | (R)IGQDGISTSATTNLK(C) (O-Gly7) | 32312 | 0 | - | 0 | 0 | - | |
| 733 | 742 | 21.5461 | (K)VLVDHFGYTK(D) (SEQ ID NO.4) | 500611 | - | - | 626235 | - | 351100 | apo B100 |
| | | 21.8974 | (K)VLVDHFGYTK(D) (O-Gly9) | 165684 | - | - | 344499 | - | 0 | |
| 1122 | 1128 | 22.3482 | (K)GVISIPR(L) (SEQ ID NO.5) | 762668 | - | - | 902565 | 847910 | - | apo B100 |
| | | 22.4782 | (K)GVISIPR(L) (O-Gly4) | 20299 | - | - | 0 | 0 | - | |
| 2241 | 2259 | 33.3865 | (K)SGSSTASWIQNVDTKYQIR(I) (SEQ ID NO.6) | | 3366 | - | - | - | - | apo B100 |
| | | | (K)SGSSTASWIQNVDTKYQIR(I) (O-Gly3) | | 0 | 62097 | - | - | - | |
| 231 | 250 | 28.1958 | (K)AKPALEDLRQGLLPVLESFK(V) (SEQ ID NO.7) | | 35561 | 0 | - | - | - | apo AI |
| | | 22.5149 | (K)AKPALEDLRQGLLPVLESFK(V) (O-Gly18) | | | | - | - | - | |

FIG. 11A

METHOD FOR EX VIVO TREATING BLOOD OR PLASMA

CROSS REFERENCE TO RELATED APPLICATION

This application is a Divisional of pending U.S. patent application Ser. No. 14/984,938, filed on Dec. 30, 2015 and entitled "BIOCHEMISTRY REACTIVE MATERIAL AND DEVICE FOR ELIMINATING ELECTRONEGATIVE LOW-DENSITY LIPOPROTEIN (LDL) AND METHOD FOR TREATING BLOOD OR PLASMA EX VIVO TO ELIMINATE ELECTRONEGATIVE LOW-DENSITY LIPOPROTEIN THEREIN" which is based on, and claims priority from, Taiwan Application Serial Number 104126050, filed on Aug. 11, 2015, and China Application Serial Number 201510815421.4, filed on Nov. 23, 2015, the disclosure of which are hereby incorporated by reference herein in its entirety.

INCORPORATION BY REFERENCE OF SEQUENCE LISTING

A sequence listing submitted as a text file via EFS-Web is incorporated herein by reference. The text file containing the sequence listing is named "0965-A24497-D1US_Seq_Listing.txt"; its date of creation was Sep. 5, 2018; and its size is 11,524 bytes.

TECHNICAL FIELD

The technical field relates to a biochemistry reactive material and device for eliminating electronegative low-density lipoprotein (LDL) and a method for treating blood or plasma ex vivo to eliminate electronegative low-density lipoprotein therein

BACKGROUND

Low-density lipoprotein (LDL) is a kind of lipoprotein that is a product of lipoprotein lipase action. Lipoproteins play a role in lipid transportation. It has long been known that the level of cholesterol carried by low-density lipoprotein is associated with the occurrence and presence of cardiovascular diseases.

At present, in the medical field, plasma LDL cholesterol (LDL-C) is still used as an indicator for estimating cardiovascular diseases. However, the low-density lipoprotein level in the plasma of patients with acute myocardial infarction has no tendency to increase.

Due to external factors, such as excess oxidation pressure, etc., low-density lipoprotein will be post-translation modified, and presents higher electronegativity to become electronegative LDL or L5.

Electronegative LDL (L5) electronegative low-density lipoprotein is a major factor for causing cardiovascular disease. L5 is almost undetectable in a normal human body. In addition, it has been in vitro and in vivo verified that L5 will damages vascular endothelial cells and activate monocytes and platelets, and result in systemic inflammation, atherosclerosis and myocardial infraction.

Therefore, a novel material, device and/or method for eliminating an electronegative low-density lipoprotein is/are needed.

SUMMARY

The present disclosure further provides a method for ex vivo treating blood or plasma, comprising (a) ex vivo contacting a blood or plasma with an enzyme composition to react the enzyme composition with the blood or plasma, wherein the enzyme composition is capable of eliminating low-density lipoprotein. The enzyme composition is selected from a group consisting of a first enzyme, a second enzyme, and a combination thereof. The first enzyme is for eliminating a glycan residue of an electronegative LDL. The second enzyme is for eliminating ceramide carried by an electronegative low-density lipoprotein. The method also comprises (b) terminating the contact between the blood or plasma and the enzyme composition to terminate the reaction of the enzyme composition with the blood or plasma.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein:

FIGS. 10A1-2 and 10B1-2 show that the mass spectrometry analysis result of L5 treated with NEU2, wherein apoE specific glycan residues have been removed;

FIGS. 11A and 11B1-4 show NEU2, NEU4 immobilized on different material both are capable of effectively eliminating glycosylation on lipoproteins; Sequences of LDL which are most commonly glycosylated comprise: 1. (R)IGQDGISTSATTNLK(C) (SEQ ID NO. 3) of apoB100; 2. (K)VLVDHFGYTK(D) (SEQ ID NO. 4) of apoB100; 3. (K)GVISIPR(L) (SEQ ID NO. 5) of apoB100; 4. (K)SGSSTASWIQNVDTKYQIR(I) (SEQ ID NO. 6) of apoB100; 5. (K)AKPALEDLRQGLLPVLESFK(V) (SEQ ID NO. 7) of apoB100. Furthermore, ITRI-A-01(NEU2), ITRI-CD-01 (NEU2), ITRI-Si-Nu-01(NEU4) all are capable of effectively eliminating glycan residues on apoB;

FIGS. 17A and 17B1-2 show that immobilized ASAH2 is capable of effectively eliminating ceramide and increasing a product, sphingosine; One of the most common ceramides of L5 is Cer (d18:0/25:0), and after it has been catalyzed by ASAH2, a product, sphingosine, is produced. The experimental results show that immobilized ASAH2 (ITRI-EC-AS-01) is capable of reducing Cer (d18:0/25:0) contained by the LDL sample and increasing the product sphingosine.

DETAILED DESCRIPTION

Figure 1A:
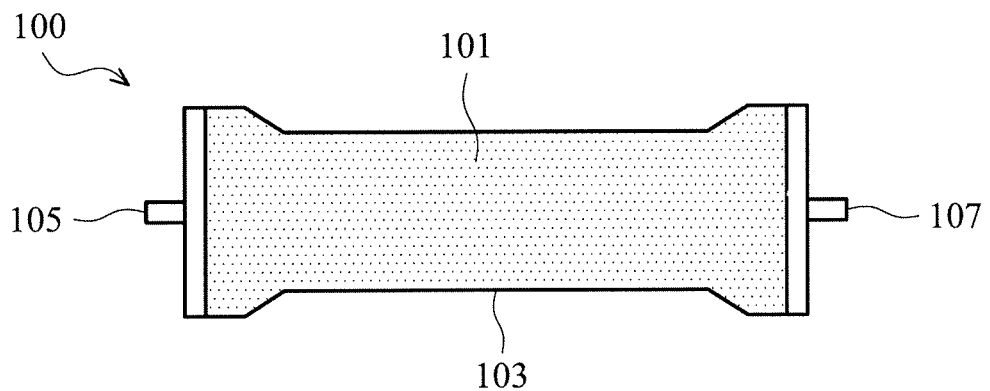
FIG. 1A is a schematic cross-sectional view of a biochemistry reactive device of one embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are shown schematically in order to simplify the drawing.

In one embodiment of the present disclosure, the present disclosure provides a biochemistry reactive material which is capable of eliminating electronegative low-density lipoprotein (electronegative LDL). Examples of the electronegative low-density lipoprotein mentioned above may comprise, but are not limited to, low-density lipoproteins L1, L2, L3, L4, L5, etc. In one embodiment, the electronegative low-density lipoprotein mentioned above may be low-density lipoprotein L5. Moreover, L5 is the most electronegative and most harmful low-density lipoprotein.

The biochemistry reactive material of the present disclosure may comprise, but is not limited to, a substrate and an enzyme composition, wherein the enzyme composition is immobilized on the substrate.

Examples of suitable substrate may comprise silica gel, cellulose, diethylaminoethyl cellulose (DEAE cellulose), chitosan, polystyrene, polysulfone, polyethersulfone, acrylate resin, polysaccharide, etc., but they are not limited thereto. The substrate may have a particle structure or a hollow-tube structure, etc. In one embodiment, the substrate may be a cellulose bead. In another embodiment, the substrate may be a chitosan bead. Moreover, the substrate may be a cellulose hollow fiber, a polysulfone hollow fiber, epoxy acrylic resin or a polyethersulfone hollow fiber, etc.

The preceding enzyme composition may comprise a first enzyme for eliminating a glycan residue of an electronegative LDL, a second enzyme for eliminating ceramide carried by an electronegative LDL, or a combination thereof, but it is not limited thereto. Source organisms of the first enzyme and the second enzyme mentioned above have no particular limitation. In one embodiment, the first enzyme and the second enzyme are bioengineered enzymes from human genome and also possibly from animal genome.

The preceding first enzyme may be sialidase or glycosidase.

The sialidase may comprise neuraminidase 1 (NEU1), neuraminidase 2 (NEU2), neuraminidase 3 (NEU3), neuraminidase 4 (NEU4) and O-sialidase bioengineered from human genome, one of the foregoing enzymes obtained through gene transformation, expression and purification, sialidase from a virus or bacterium (alias, acetylneuraminyl hydrolase), etc., but it is not limited thereto.

Examples of the glycosidase may comprise alpha- and beta-glucosidase bioengineered from human or animal genome, maltase-glucoamylase and sucrase-isomaltase, one of the foregoing enzymes obtained through gene transformation, expression and purification, N-glycosidase F (PN-Gase F) and glucosidase from a virus, a bacterium or other organism, etc., but they are not limited thereto.

Furthermore, the second enzyme may be ceramidase.

The ceramidase may comprise N-acylsphingosine amidohydrolase 1 (ASAH1), N-acylsphingosine amidohydrolase 2 (ASAH2), N-acylsphingosine amidohydrolase 2B (ASAH2B), N-acylsphingosine amidohydrolase 2C (ASAH2C), N-acylethanolamine acid amidase, alkaline ceramidase 1, alkaline ceramidase 2, alkaline ceramidase 3, but it is not limited thereto.

In one embodiment, the enzyme composition in the biochemistry reactive material of the present disclosure is the first enzyme. In this embodiment, the first enzyme mentioned above may be sialidase, but it is not limited thereto.

In another embodiment, the enzyme composition in the biochemistry reactive material of the present disclosure is the second enzyme. In this embodiment, the second enzyme mentioned above may be N-acylsphingosine amidohydrolase 2, but it is not limited thereto.

In another embodiment, the enzyme composition in the biochemistry reactive material of the present disclosure is a combination of the first enzyme and the second enzyme. In this embodiment, the first enzyme mentioned above may be sialidase, but it is not limited thereto, and the second enzyme mentioned above may be N-acylsphingosine amidohydrolase 2, but it is not limited thereto.

In another embodiment of the present disclosure, the present disclosure provides a biochemistry reactive device, and the device can be used for eliminating electronegative low-density lipoprotein in a liquid sample.

Examples of the foregoing liquid sample may comprise an aqueous solution, a buffer, blood, plasma, etc., but they are not limited thereto.

Examples of the foregoing electronegative low-density lipoprotein may comprise electronegative low-density lipoprotein L1, L2, L3, L4 and/or L5, etc., but they are not limited thereto. In one embodiment, the electronegative low-density lipoprotein mentioned above may be electronegative low-density lipoprotein L5.

Figures 1, 10A:
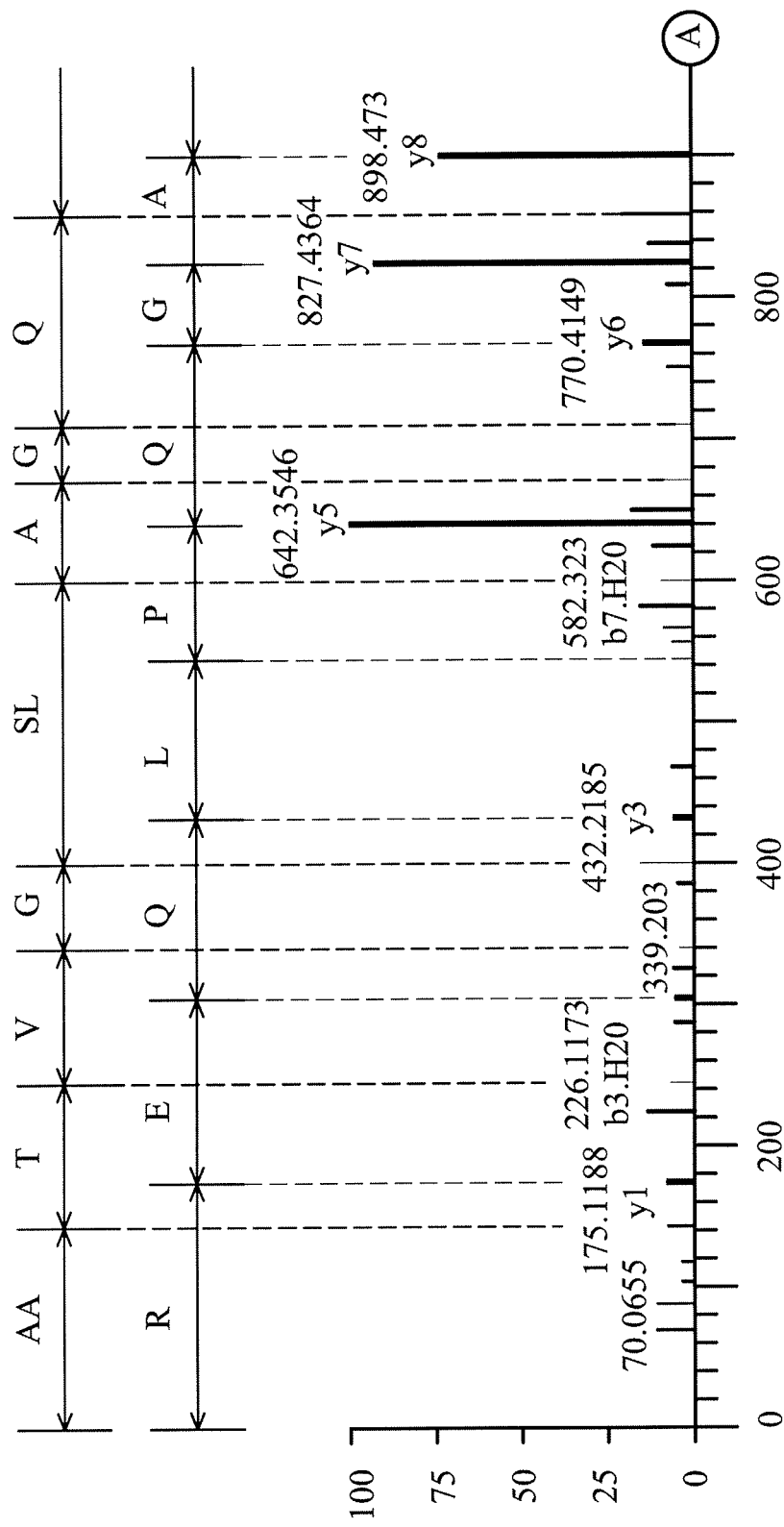
Figures 2, 10A:
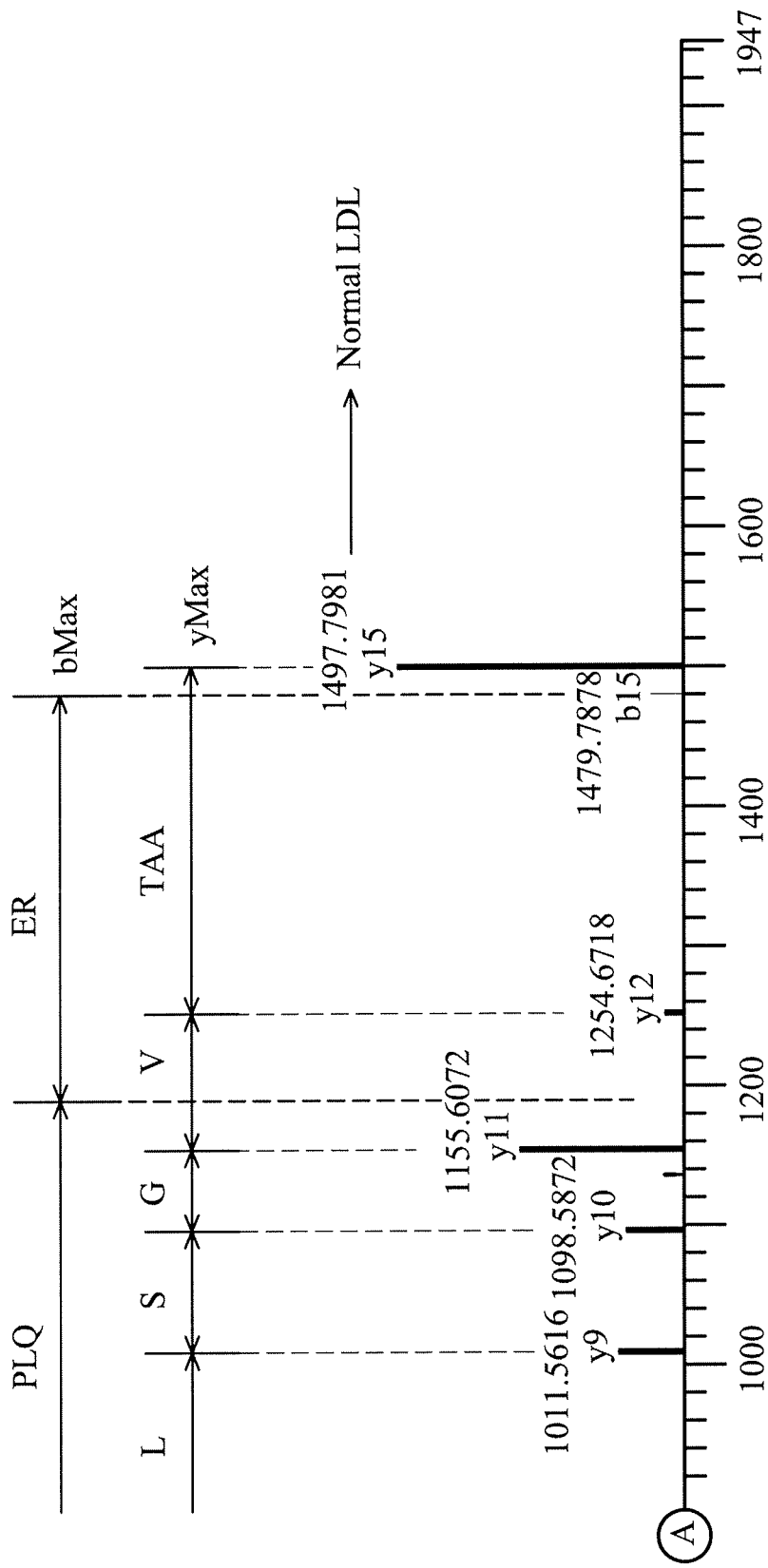

A cross-sectional view of a structure of the biochemistry reactive device of the present disclosure is shown in FIG. 1.

Refer to FIG. 1A. The preceding biochemistry reactive device of the present disclosure 100 may comprise a biochemistry reactive material 101 and a container 103 for containing the biochemistry reactive material 101. The container 103 has at least one inlet 105 and at least one outlet 107. The foregoing liquid sample enters into the biochemistry reactive device 100 from the inlet 105, and flows through the biochemistry reactive material 101 to react with the biochemistry reactive material 101, and then flows out through the outlet 107.

The biochemistry reactive material 101 may comprise, but is not limited to a substrate and an enzyme composition, wherein the enzyme composition is immobilized on the substrate.

The substrate mentioned above may comprise, but is not limited to, silica gel, cellulose, diethylaminoethyl cellulose, chitosan, polystyrene, polysulfone, polyethersulfone, acrylate resin, polysaccharide, etc. The substrate may have a particle structure or a hollow-tube structure, etc., but it is not limited thereto.

The enzyme composition may comprise, but is not limited to, a first enzyme for eliminating a glycan residue of an electronegative LDL, a second enzyme for eliminating ceramide carried by an electronegative LDL or a combination thereof. Source organisms of the first enzyme and the second enzyme mentioned above have no particular limitation. In one embodiment, the first enzyme and the second enzyme are human.

The preceding first enzyme may be sialidase or glycosidase.

The sialidase may comprise, but is not limited to, neuraminidase 1 (NEU1), neuraminidase 2 (NEU2), neuraminidase 3 (NEU3), neuraminidase 4 (NEU4) and O-sialidase bioengineered from human genome, one of the foregoing enzymes obtained through gene transformation, expression and purification, sialidase from a virus, a bacterium or other organism, etc.

The glycosidase may comprise, but is not limited to, alpha- and beta-glucosidase bioengineered from human or animal genome, maltase-glucoamylase and sucrase-isomaltase, one of the foregoing enzymes obtained through gene transformation, expression and purification, N-glycosidase F (PNGase F) and glucosidase from a virus, a bacterium or other organism, etc.

In addition, the second enzyme may be ceramidase. The ceramidase may comprise, but is not limited to, N-acylsphingosine amidohydrolase 1 (ASAH1), N-acylsphingosine amidohydrolase 2 (ASAH2), N-acylsphingosine amidohydrolase 2B (ASAH2B), N-acylsphingosine amidohydrolase 2C (ASAH2C), N-acylethanolamine acid amidase, alkaline ceramidase 1, alkaline ceramidase 2, alkaline ceramidase 3.

In one embodiment, the enzyme composition in the biochemistry reactive material 101 mentioned above is the first enzyme. In this embodiment, the first enzyme mentioned above may be sialidase, but it is not limited thereto.

In another embodiment, the enzyme composition in the biochemistry reactive material 101 mentioned above is the second enzyme. In this embodiment, the second enzyme mentioned above may be N-acylsphingosine amidohydrolase 2, but it is not limited thereto.

In another embodiment, the enzyme composition in the biochemistry reactive material 101 mentioned above is a combination of the first enzyme and the second enzyme. In this embodiment, the first enzyme mentioned above may be sialidase, but it is not limited thereto, and the second enzyme mentioned above may be N-acylsphingosine amidohydrolase 2, but it is not limited thereto.

Furthermore, a material of the container 103 of the biochemistry reactive device 100 of the present disclosure may comprise glass, acrylic, polypropylene, polyethylene, stainless steel, titanium alloy, etc., but it is not limited thereto. In one embodiment, a material of the container 103 of the biochemistry reactive device 100 of the present disclosure may be polypropylene. In addition, a shape of the container 103 has no particular limitation, and in one embodiment, the container 103 is a hollow column.

Figure 1B:
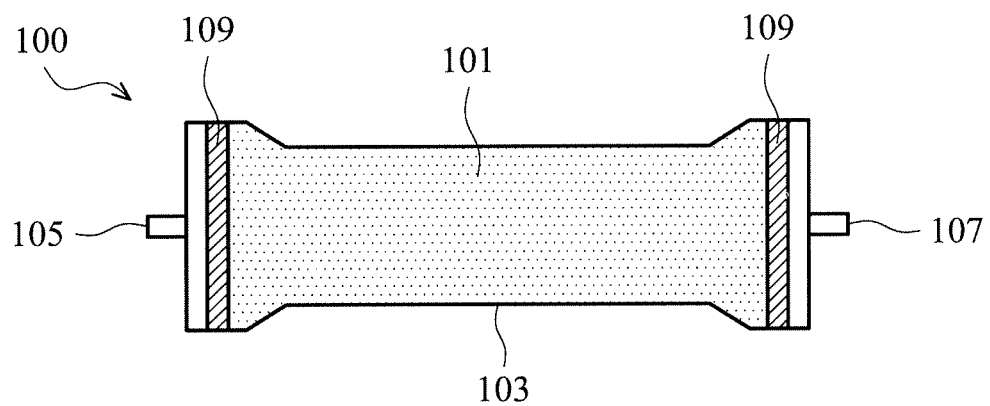
FIG. 1B is a schematic cross-sectional view of a biochemistry reactive device of another embodiment of the present disclosure.

In one embodiment, as shown in FIG. 1B, the biochemistry reactive device 100 of the present disclosure may further comprise a filtering material 109 configured in the container 103 behind the at least one inlet 105 and at least one outlet 107. Moreover, the pore size of the filtering material mentioned above is smaller than the biochemistry reactive material 101 to prevent the biochemistry reactive material 101 leaking from the at least one inlet 105 and/or least one outlet 107, but it can allow the liquid sample to pass through. The filtering material 109 mentioned above comprises filter paper, glass, acrylic, polypropylene, polyethylene, etc., but it is not limited thereto. In this embodiment, the substrate of the biochemistry reactive material 101 may have a particle structure or a hollow-tube structure. In one specific embodiment, the substrate of the biochemistry reactive material 101 has a particle structure, and in this specific embodiment, the substrate of the biochemistry reactive material 101 may be a cellulose bead or a chitosan bead, but it is not limited thereto.

When the substrate of the biochemistry reactive material 101 is a hollow-tube structure, polyurethane (PU) can be used to package the device without using the filtering material 109.

In one embodiment, the container 103 may be a hollow column, and two ends of the hollow column of the container 103 have a first inlet $105_1$ of the inlet mentioned above and a first outlet $107_1$ of the outlet mentioned above, respectively. In this embodiment, the substrate of the biochemistry reactive material 101 may have a particle structure or a hollow-tube structure.

Figure 1C:
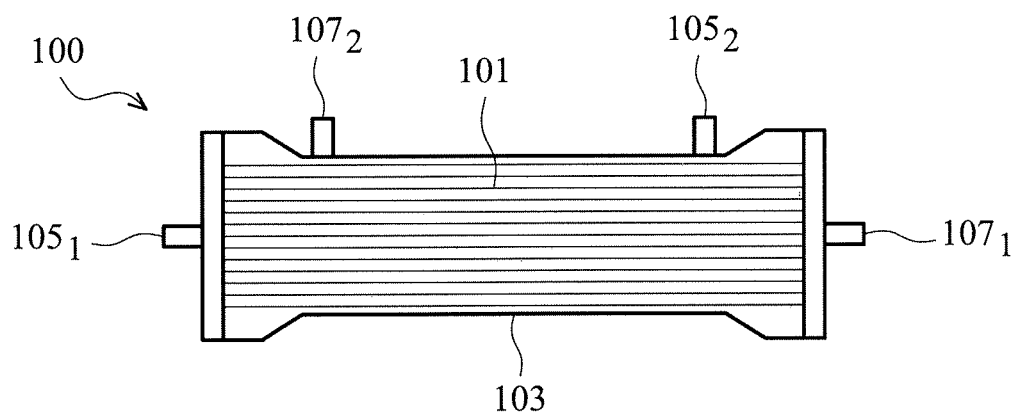
FIG. 1C is a schematic cross-sectional view of a biochemistry reactive device of another embodiment of the present disclosure.

In another embodiment, as shown in FIG. 1C, the container 103 may be a hollow column, and two ends of the hollow column of the container 103 have a first inlet $105_1$ of the inlet mentioned above and a first outlet $107_1$ of the at least outlet mentioned above, respectively, and a second inlet $105_2$ of the inlet and a second outlet $107_2$ of the outlet are located at a side wall of the hollow column. In this embodiment, the liquid sample can enter into the biochemistry reactive device 100 from the first inlet $105_1$ of the container 103, and flows through the biochemistry reactive material 101, and then flows out through the first outlet $107_1$. Moreover, a second liquid which can be water, a dialysis solution or a salt-containing aqueous solution enters into the biochemistry reactive device 100 from the first inlet $105_2$, and flows through the biochemistry reactive material 101, and then flows out through the first outlet $107_2$. The second liquid can bring a by-product out after the reaction or dialysis.

In this embodiment, the substrate of the biochemistry reactive material 101 may have a particle structure or a hollow-tube structure. In one specific embodiment, the substrate of the biochemistry reactive material 101 has a hollow-tube structure, and in this specific embodiment, the substrate of the biochemistry reactive material 101 may be cellulose hollow fiber, but it is not limited thereto.

In another embodiment of the present disclosure, the present disclosure provides a method for ex vivo treating blood or plasma. By the method for ex vivo treating blood or plasma, an electronegative low-density lipoprotein in blood or plasma can be eliminated. The foregoing electronegative low-density lipoprotein may comprise, but is not limited to, electronegative low-density lipoprotein L1, L2, L3, L4 and/or L5, etc. In one embodiment, the electronegative low-density lipoprotein mentioned above is electronegative low-density lipoprotein L5.

The method for ex vivo treating blood or plasma may comprise the following steps, but it is not limited thereto.

First, a blood or plasma ex vivo contacts with an enzyme composition to react the enzyme composition with the blood or plasma, wherein the enzyme composition is capable of eliminating electronegative low-density lipoprotein.

The preceding enzyme composition may comprise a first enzyme for eliminating a glycan residue of an electronegative LDL, a second enzyme for eliminating ceramide carried by an electronegative LDL or a combination thereof, but it is not limited thereto. Source organisms of the first enzyme and the second enzyme mentioned above have no particular limitation. In one embodiment, the first enzyme and the second enzyme are human.

The preceding first enzyme may be sialidase or glycosidase.

The sialidase may comprise neuraminidase 1 (NEU1), neuraminidase 2 (NEU2), neuraminidase 3 (NEU3), neuraminidase 4 (NEU4) and O-sialidase from a human, or one of the foregoing enzymes obtained through gene transformation, expression and purification, sialidase from a virus, a bacterium or other organisms, etc., but it is not limited thereto.

Examples of the glycosidase may comprise alpha- and beta-glucosidase bioengineered from human animal genome, maltase-glucoamylase and sucrase-isomaltase, one of the foregoing enzymes obtained through gene transformation, expression and purification, N-glycosidase F (PNGase F) and glucosidase from a virus, a bacterium or other organism, etc., but they are not limited thereto.

Furthermore, the second enzyme mentioned above may be ceramidase.

The ceramidase may comprise N-acylsphingosine amidohydrolase 1 (ASAH1), N-acylsphingosine amidohydrolase 2 (ASAH2), N-acylsphingosine amidohydrolase 2B (ASAH2B), N-acylsphingosine amidohydrolase 2C (ASAH2C), N-acylethanolamine acid amidase, alkaline ceramidase 1, alkaline ceramidase 2, alkaline ceramidase 3, but it is not limited thereto.

In one embodiment, the enzyme composition used in the method for ex vivo treating blood or plasma of the present disclosure is the first enzyme. In this embodiment, the first enzyme mentioned above may be sialidase, but it is not limited thereto.

In another embodiment, the enzyme composition used in the method for ex vivo treating blood or plasma of the present disclosure is the second enzyme. In this embodiment, the second enzyme mentioned above may be N-acylsphingosine amidohydrolase 2, but it is not limited thereto.

In another embodiment, the enzyme composition used in the method for ex vivo treating blood or plasma of the present disclosure is a combination of the first enzyme and the second enzyme. In this embodiment, the first enzyme mentioned above may be sialidase, but it is not limited thereto, and the second enzyme mentioned above may be N-acylsphingosine amidohydrolase 2, but it is not limited thereto.

Furthermore, in one embodiment, the enzyme composition used in the method for ex vivo treating blood or plasma of the present disclosure can be immobilized on a substrate. Examples of the substrate may comprise silica gel, cellulose, diethylaminoethyl cellulose, chitosan, polystyrene, polysulfone, polyethersulfone, resin, polysaccharide, but they are not limited thereto. Moreover, the substrate may have a particle structure or a hollow-tube structure.

In the method for ex vivo treating blood or plasma of the present disclosure, time for ex vivo contacting the blood or plasma with the enzyme composition may be about 0.25-8 hours. In one embodiment, time for ex vivo contacting the blood or plasma with the enzyme composition may be about 2 hours.

Furthermore, in the method for ex vivo treating blood or plasma of the present disclosure, temperature for ex vivo contacting the blood or plasma with the enzyme composition may be about 4-40° C. In one embodiment, temperature for ex vivo contacting the blood or plasma with the enzyme composition may be about 37° C.

In addition, in the method for ex vivo treating blood or plasma of the present disclosure, the blood or plasma may ex vivo contact with the enzyme composition at about pH 5-10. In one embodiment, the blood or plasma may ex vivo contact with the enzyme composition at about pH 7.4.

Afterward, contact between the blood or plasma and the enzyme composition is terminated to terminate the reaction of the enzyme composition with the blood or plasma.

A manner for terminating the contact between the blood or plasma and the enzyme composition has no particular limitation, for example, for terminating the contact between the blood or plasma and the enzyme composition, the blood or plasma can be separated from the enzyme composition, or the enzyme composition can be deactivated, etc.

EXAMPLES

Example 1

A. Methods

1. Obtainment of Electronegative Low-Density Lipoprotein (Electronegative LDL)

(1) Purifications for Electronegative Low-Density Lipoprotein

Blood samples to be used for LDL isolation were obtained from subjects. After the initial screening, blood samples were removed from the subjects with precaution against coagulation and ex vivo oxidation. The plasma was treated with Complete Protease Inhibitor Cocktail (Roche; Cat. No. 05056489001; 1 tablet/100 mL) to prevent protein degradation.

Lipoprotein Preparation from a Human

The plasma was overlaid with 2 mL Milli-Q water and spun at 20,000 rpm for 2 hours. The upper white fraction and chylomicrons were removed, and the remnant layer which contains VLDL, IDL, LDL and HDL was saved for a series of isolation steps.

To progressively separate VLDL (d=0.93-1.006), IDL (d=1.006-1.019), LDL (1.019-1.063 g/dL) and HDL (1.063-1.210 g/dL) from one another, the remnant sample was sequentially adjusted to d=1.006, d=1.019, d=1.063, d=1.210, respectively, by adding potassium bromide, and then the remnant samples sequentially adjusted to d=1.006, d=1.019 and d=1.063 were centrifuged at 45,000 rpm for 24 hours at 4° C., and the remnant sample sequentially adjusted to d=1.210 was centrifuged at 45,000 rpm for 48 hours at 4° C. After centrifugation at each isolation step, IDL was discarded while VLDL, LDL and HDL were collected. Isolated VLDL, LDL and HDL samples were treated with 5 mM EDTA and nitrogen to avoid ex vivo oxidation. After that, VLDL, LDL and HDL samples were dialyzed against buffer A (20 M, pH 8.0, 0.5 M EDTA) for 24 hours (×3 times) to remove excessive potassium bromide, and were filtrated through 0.22-μm filter (Sartorius; Minisart®) to sterilize the samples.

(2) LDL Subfractions

Approximately 30 mg of LDL material was injected onto a UnoQ12 anion-exchange column (BioRad) by using the ÄKTA fast-protein liquid chromatography (FPLC) pump (GE Healthcare Life Sciences, Pittsburgh, Pa.). LDL was eluted according to electronegativity by the use of a multi-step gradient of buffer B (1 mol/L NaCl in buffer A) at a flow rate of 2 mL/minute. In short, samples were equilibrated with buffer A for 10 minutes, followed by being linearly increased to 15% buffer B in 10 minutes (fraction 1), linearly increased to 20% buffer B in 30 minutes (fraction 2, 3), kept at 20% buffer B for 10 minutes (fraction 4) and linearly increased to 100% buffer B in 20 minutes (fraction 5). Lastly, the effluents were monitored at 280 nm.

(3) Purification of Fractionated LDL

Based on the gradient profile, each of the LDL fractions were pooled. The volume of each subfraction was constant. Dilution of LDL during chromatography depended on the injection volume. The respective fractions were concentrated with Centriprep® filters (YM-30; EMD Millipore Corp., Billerica, Mass.), dialyzed against buffer A (20 M, pH8.0, 0.5 M EDTA) for 24 hours (3 days) and sterilized by passing through 0.22-μm filters (Sartorius; Minisart®). The isolated fractions were quantified at their protein concentrations by the Lowry method and then stored at 4° C.

2. Screening of NEU2 or NEU4

(1) Transformation (Gene Cloning for pCMV6 Vector with NEU2 and NEU4 Genes)

NEU2 (neuraminidase 2) and NEU4 (neuraminidase 4) were purchased from Origene, RC219858 and RC203948. Genes were amplified by ECOSTM 101 DH5α Competent Cells (Yeastern, FYE608) according to the manufacturer's directions.

In short, 1 vial of competent cells with 5 μL plasmid was vortexed for 1 second and then incubated on ice for 5 minutes. After 45 second heat-shock at 42° C., the mixture was plate on LB agar with Kanamycin.

Colonies were checked with PCR by VP1.5 and XL39 primers. Procedures of the PCR comprises: 95° C. for 1 minute for pre-PCR denaturation; 2 cycles of 95° C. for 10 seconds, 62° C. for 20 seconds, 72° C. for 4 minutes; 2 cycles of 95° C. for 10 seconds, 60° C. for 20 seconds, 72° C. for 4 minutes; 2 cycles of 95° C. for 10 seconds, 58° C. for 20 seconds, 72° C. for 4 minutes; 15 cycles of 95° C. for 10 seconds, 56° C. for 20 seconds, 72° C. for 4 minutes; 72° C. for 10 minutes for post-PCR incubation and holding on 4° C.

(2) Plasmid Extraction

After confirming the insertion of transformed colonies, transformed cells were plate-out into 5 ml LB broth with 25 mg/ml kanamycin, and then incubated at 37° C. overnight.

Plasmid DNA was extracted according to the protocol of Plasmid Miniprep Plus Purification Kit (GeneMark, DP01P). In short, the bacteria were centrifuged for 1 minute at 14,000×g, and the media was removed. The pellet was re-suspended in 200 μL Solution I by pipetting, then 200 μL Solution II was added therein and mixed by inverting the tube. 200 μL Solution III was added to the tube and mixed by inverting the tube 5 times. The lysate was centrifuged at top speed for 5 minutes and a compact white pellet formed along the side of the tube. The spin column was inserted into a collection tube, and the clear lysate was moved to spin column and spun at top speed for 1 minute. The flow-through was discarded, and 500 μL Endotoxin Removal Wash Solution was loaded to the spin column and kept for 2 minutes to equilibrate the membrane, then spun at top speed for 1 minute. The filtrate was discarded, and 700 μL Washing Solution was added to the spin column and spun at top speed for 1 minute, and then this step was repeated. The filtrate was discarded and the spin column was centrifuged for 5 minutes at top speed to remove residual traces of ethanol. The spin column was transferred into a new tube and 35 μL $H_2O$ was added to the spin column and kept for 1-2 minutes and the tube was centrifuged at top speed for 2 minutes to elute the DNA. The DNA quantified by microplate spectrophotometer (Epoch, BioTek).

(3) Transfection on HEK Cells and Protein Purification

One day before transfection, $1.25*10^5$ HEK293T cells were placed in 500 μL DMEM medium in 24-well plate. For each well of cells to be transfected, 1 μg of DNA was diluted in 100 μL serum-free medium, and 1.5 μL of Lipofectamine 2000 Transfection Reagent (Invitrogen) was add thereto and mixed gently and incubated for 30 minutes at room temperature. After incubation, the complex was added to each well containing cells and mixed gently. The cells were incubated at 37° C. in a $CO_2$ incubator for 20 hours. The transfected cells were lysed by RIPA which containing protease inhibitor to prepare to purify the proteins.

In short, 80 μL ANTI-FLAG M2 Magnetic Beads (Sigma-Aldrich) were equilibrated for one-well cell lysate purification. After protein-resin binding at 4° C. overnight, the bound FLAG fusion protein was eluted by competitive elution with 150 μg/ml 3×FLAG peptide for 2 times, the eluate was collected, and the protein checked by western blot.

3. Efficacy Test for NEU2 or NEU4

(1) Protein Quantification

Pierce BCA Protein Assay Kit (Thermo) was used for protein quantification according to the manufacturer's directions.

In short, 25 μL serial diluted BSA standard and 5 μL sample in 20 μL sample diluent were pipetted into a 96-well microplate. To prepare BCA working reagent, 50 parts of BCA Reagent A was mixed with 1 part of BCA Reagent B and placed on ice until use. 200 μL of the BCA working reagent was added to each well and mixed thoroughly, and the plate was covered and incubated at 37° C. for 30 minutes. The absorbance at 562 nm was measured by spectrophotometer (Epoch, BioTek).

(2) Apoptosis Measurements

Endothelial cells were used after 3 or 4 passages and maintained in DMEM (Invitrogen™, Thermo Fisher Scientific) containing 10% FBS. During treatment, FBS was reduced to 5% in DMEM. $1\times10^4$ cells were seeded in 96-well plate for 24 hours for subconfluent cultures, and the cultured cells were exposed to PBS (lipoprotein-free, negative control) or graded (25, 50, and 100 μg/mL) LDL subfractions, unfractionated normolipidemic LDL, and LDL/L1/L5 incubated with sialidase for 24 hours. Apoptosis was assessed with visualization by a Zeiss Axiovert 200 fluorescence microscope and filters to capture digital images based on Hoechst 33342, propidium iodide (red), and calcein AM (green) staining of nuclear, apoptotic DNA membrane integrity and cytoplasm respectively according to the protocol of the manufacturer (Invitrogen™, Thermo Fisher Scientific).

(3) $LC/MS^E$ Analysis for Protein Composition

LDL subfractions were quantified the protein contents by use of quantitative proteomics techniques utilizing serially coupled liquid chromatography data-independent parallel-fragmentation mass spectrometry ($LC/MS^E$). Such analysis has been shown to be highly quantitative with respect to both relative and/or absolute (when incorporating spiked internal peptide standards in the data collection/analysis procedures) protein abundance in complex protein mixtures. Quantitative analysis was performed essentially as previously described (PMCID: PMC3816395; Pure Appl Chem. 2011;

83(9): 10.1351/PAC-CON-10-12-07. Chemical composition-oriented receptor selectivity of L5, a naturally occurring atherogenic low-density lipoprotein), except on a Waters nanoACQUITY UPLC System and Xevo® G2-XS QTof mass spectrometer (Waters Corporation, MA, USA).

In brief, total proteins isolated from each LDL subfraction were first digested with trypsin, and the resulting tryptic peptides were chromatographically separated on a Nano-Acquity separations module (Waters Corporation, MA, USA) incorporating a 50 fmol-on-column tryptic digest of yeast alcohol dehydrogenase as the internally spiked protein quantification standard. Peptide elution will be executed through a 75 im×25 cm BEH C-18 column under gradient conditions at a flow rate of 300 nL/minute over 30 minutes at 35° C. The mobile phase was composed of acetonitrile as the organic modifier and formic acid (0.1% v/v) for molecule protonation. Mass spectrometry was performed on a Xevo® G2-XS QTof instrument equipped with a nano-electrospray ionization interface and operated in the data-independent collection mode (MSE). Parallel ion fragmentation was programmed to switch between low (4 eV) and high (15-45 eV) energies in the collision cell, and data was collected from 50 to 2000 m/z utilizing glu-fibrinopeptide B as the separate data channel lock mass calibrant. Data was processed with ProteinLynx GlobalServer v2.4 (Waters). Deisotoped results were searched for protein association from the Uniprot (www.uniprot.org) human protein database.

4. Screening of ASAH2

(1) Transformation (Gene Cloning for pCMV6 Vector with ASAH2 Genes):

ASAH2 (N-acylsphingosine amidohydrolase 2) was purchased from Origene, RC203706. Genes were amplified by ECOSTM 101 DH5α Competent Cells (Yeastern, FYE608) according to the manufacturer's directions.

In short, 1 vial of competent cells with 5 μL plasmid was vortexed for 1 second and then incubated on ice for 5 minutes. After 45 second heat-shock at 42° C., the mixture was plate on LB agar with Kanamycin.

Colonies were checked with PCR by VP1.5 and XL39 primers. Procedures of the PCR comprise: 95° C. for 1 minute for pre-PCR denaturation; 2 cycles of 95° C. for 10 seconds, 62° C. for 20 seconds, 72° C. for 4 minutes; 2 cycles of 95° C. for 10 seconds, 60° C. for 20 seconds, 72° C. for 4 minutes; 2 cycles of 95° C. for 10 seconds, 58° C. for 20 seconds, 72° C. for 4 minutes; 15 cycles of 95° C. for 10 seconds, 56° C. for 20 seconds, 72° C. for 4 minutes; 72° C. for 10 minutes for post-PCR incubation and holding on 4° C.

(2) Plasmid Extraction

After confirming the insertion of transformed colonies, transformed cells were plate-out into 5 ml LB broth with 25 mg/ml kanamycin, and then incubated at 37° C. overnight.

Plasmid DNA was extracted according to the protocol of Plasmid Miniprep Plus Purification Kit (GeneMark, DP01P). In short, the bacteria were centrifuged for 1 minute at 14,000×g, and the media was removed. The pellet was re-suspended in 200 μL Solution I by pipetting, then 200 μL Solution II was added therein and mixed by inverting the tube. 200 μL Solution III was added to the tube and mixed by inverting the tube 5 times. The lysate was centrifuged at top speed for 5 minutes and a compact white pellet formed along the side of the tube. The spin column was inserted into a collection tube, and the clear lysate was removed to spin column and spun at top speed for 1 minute. The flow-through was discarded, and 500 μL Endotoxin Removal Wash Solution was loaded to the spin column and kept for 2 minutes to equilibrate the membrane, then spun at top speed for 1 minute. The filtrate was discarded, and 700 μL Washing Solution was added to the spin column and spun at top speed for 1 minute, and then this step was repeated. The filtrate was discarded and the spin column was centrifuged for 5 minutes at top speed to remove residual traces of ethanol. The spin column was transferred into a new tube and 35 μL H2O was added to the spin column and kept for 1-2 minutes and the tube was centrifuged at top speed for 2 minutes to elute the DNA. The DNA quantified by microplate spectrophotometer (Epoch, BioTek).

(3) Transfection on HEK Cells and Protein Purification

One day before transfection, $1.25*10^5$ HEK293T cells were placed in 500 μL DMEM medium in 24-well plate. For each well of cells to be transfected, 1 μg of DNA was diluted in 100 μL serum-free medium, and 1.5 μL of Lipofectamine 2000 Transfection Reagent (Invitrogen) was add thereto and mixed gently and incubated for 30 minutes at room temperature. After incubation, the complex was added to each well containing cells and mixed gently. The cells were incubated at 37° C. in a $CO_2$ incubator for 20 hours. The transfected cells were lysed by RIPA which containing protease inhibitor to prepare to purify the proteins.

In short, 80 μL ANTI-FLAG M2 Magnetic Beads (Sigma-Aldrich) were equilibrated for one-well cell lysate purification.

After protein-resin binding at 4° C. overnight, the bound FLAG fusion protein was eluted by competitive elution with 150 μg/ml 3×FLAG peptide for 2 times, the eluate was collected, and the protein checked by western blot.

5. Efficacy Test for ASAH2

(1) Protein Quantification

Pierce BCA Protein Assay Kit (Thermo) was used for protein quantification according to the manufacturer's directions.

In short, 25 μL serial diluted BSA standard and 5 μL sample in 20 μL sample diluent were pipetted into a 96-well microplate. To prepare BCA working reagent, 50 parts of BCA Reagent A was mixed with 1 part of BCA Reagent B and placed on ice until use. 200 μL of the BCA working reagent was added to each well and mixed thoroughly, and the plate was covered and incubated at 37° C. for 30 minutes. The absorbance at 562 nm was measured by spectrophotometer (Epoch, BioTek).

(2) Lipid Extraction

30 μg LDL/L1/L5 were incubated with 5 μg ASAH2 in ASAH2 buffer (200 mM Tris-HCl at pH 8.4, 1.5 M NaCl, 25 mM $CaCl_2$) at 37° C. After 2 or 24 hours incubation, samples were transferred to a glass tube. I mL $H_2O$, 2.5 mL methanol and 1.25 mL $CHCl_3$ were added to samples, and vortexed for 15 seconds. Then, additional 0.9 mL $H_2O$ and 1.25 mL $CHCl_3$ were applied to samples, vortexed for 15 seconds, and centrifuged at 3000 rpm for 10 minutes. Bottom layer organic solvents were transferred to a 2.0 mL glass tube using a glass syringe. Each sample was flushed with nitrogen until dry pallets, and dissolved with 0.25 mL sample solution (isopropanol/acetonitrile/$H_2O$=2:1:1).

(3) LC/$MS^E$ Analysis for Lipid Composition

Total lipids, phospholipids, neutral lipids and free fatty acid from each subfractions of LDL were quantified the lipid contents by use of liquid chromatography data-independent parallel-fragmentation mass spectrometry (LC/$MS^E$). Quantitative analysis was performed essentially as previously described.

In brief, lipids were chromatographically separated on a ACQUITY UPLC System (Waters Corporation, MA, USA) incorporating a CSH™ 1.7 μm, 2.1 mm×10 cm C-18 column under gradient conditions at a flow rate of 400 μL/minute over 18 minutes at 55° C. The mobile phase A will be composed of 10 mM NH4HCO$_2$ in ACN/H$_2$O (60/40) and 0.1% formic acid (0.1% v/v), mobile phase B will be composed of 10 mM NH$_4$HCO$_2$ in IPA/ACN (90/10) and 0.1% formic acid (0.1% v/v) for molecule protonation. Mass spectrometry was performed on a Xevo® G2-XS QT of instrument equipped with an electrospray ionization interface and operated in the data-independent collection mode (MSE). Parallel ion fragmentation was programmed to switch between low (4 eV) and high (35-55 eV) energies in the collision cell, and data was collected from 50 to 1600 m/z utilizing leucin as the separate data channel lock mass calibrant. Data was processed with MarkerLynx (Waters).

B. Results

1. Transformation (1) NEU2

Figure 2:
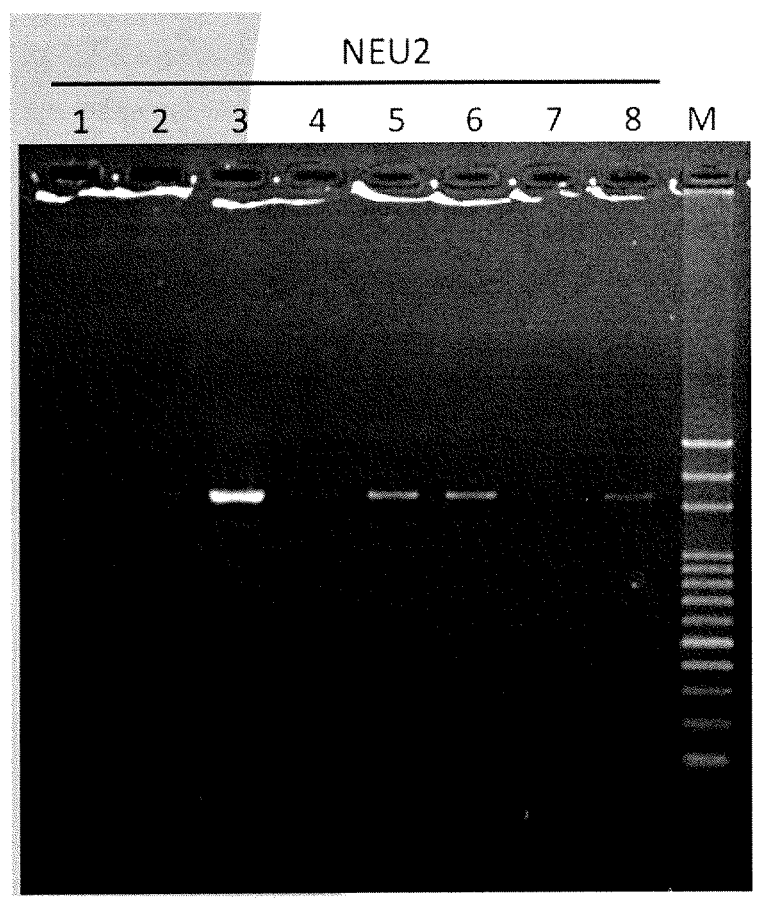
FIG. 2 shows the transformation result for NEU2.

Transformation result for NEU2 is shown in FIG. 2.

According to FIG. 2, it is known that NEU2 transformations for colonies 3, 5 and 6 (see lane 3, 5 and 6, respectively) were successful. Therefore, colonies 3, 5 and 6 were selected to be amplified, and plasmid of NEU2 was stocked.

(2) ASAH2

Figure 3:
FIG. 3 shows the transformation result for ASAH2.

Transformation result for ASAH2 is shown in FIG. 3.

Colony 7 was selected to be amplified, and plasmid of ASAH2 was stocked.

2. Transfection

Figure 4:
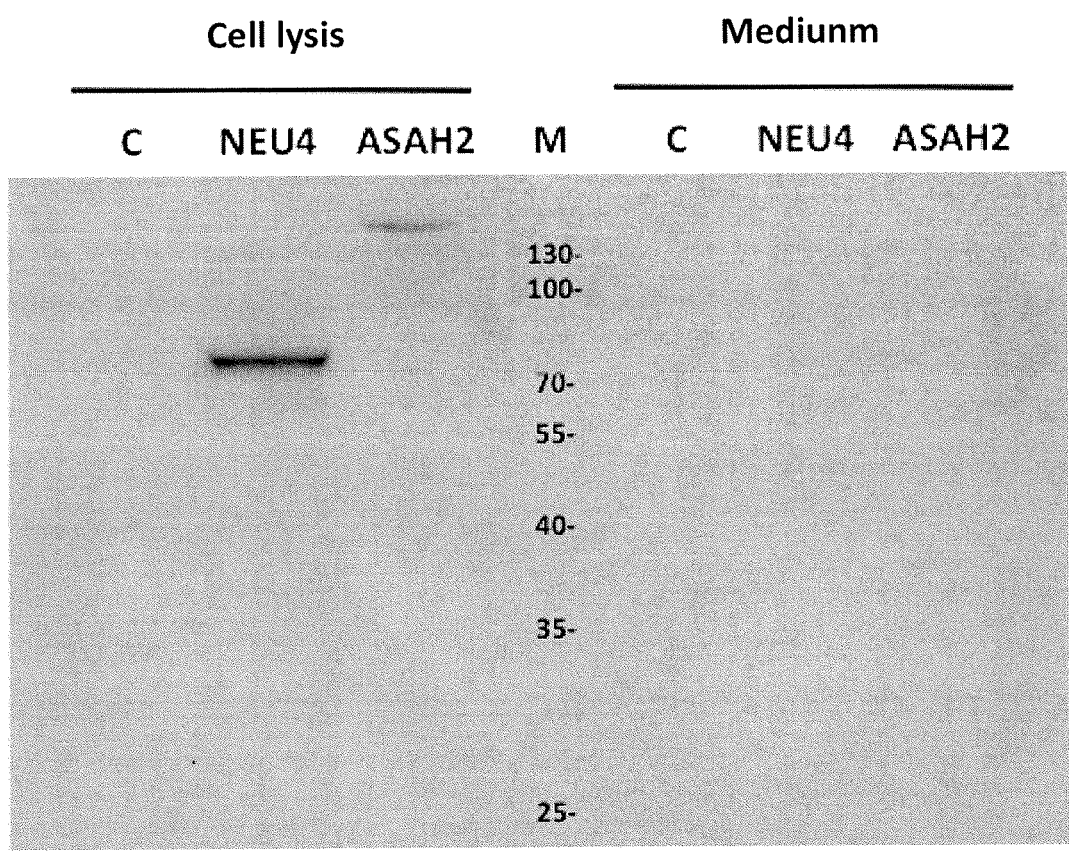
FIG. 4 shows the result of gene transfection of NEU4/ASAH2 confirmed by western blot.

Transfection of NEU4/ASAH2 genes was confirmed by western blot, and the result is shown in FIG. 4.

Conditions for the gene transfection are shown in the following:

HEK293T 1.25×10$^5$ cells in 24 well
Plasmid: NEU4 and ASAH2
DNA amount: 1 μg
Transfected by Lipofectamine
SDS-PAGE: using 5 μl sample
Primary antibody: anti-DDK (1:2000)

3. Protein Purification (1) NEU2 Purification

Figure 5:
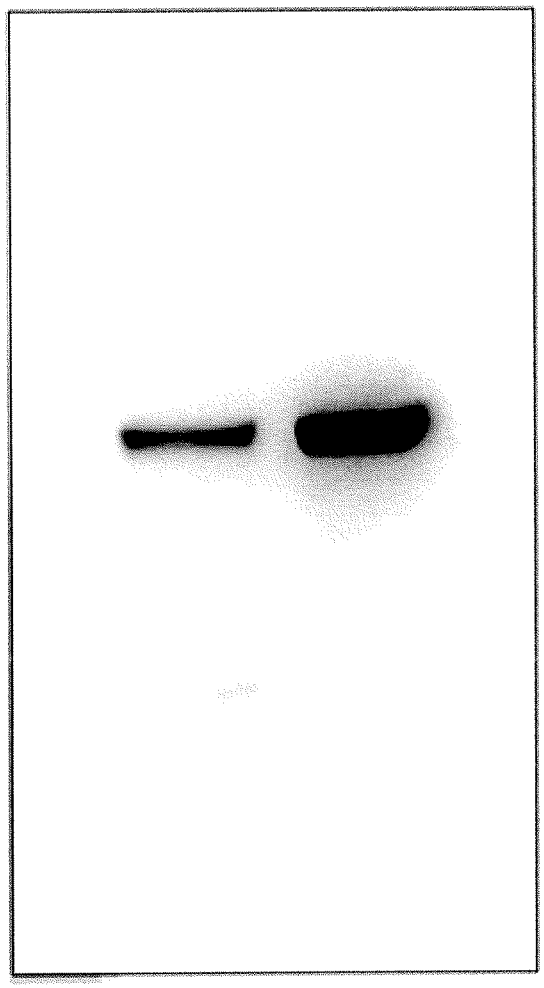
FIG. 5 shows the result for NEU2 purification.

The result for NEU2 purification is shown in FIG. 5. FIG. 5 shows that NEU2 was indeed purified. The amino acid sequence of NEU2 is shown as SEQ ID NO. 1.

(2) ASAH2 Purification

Figure 6:
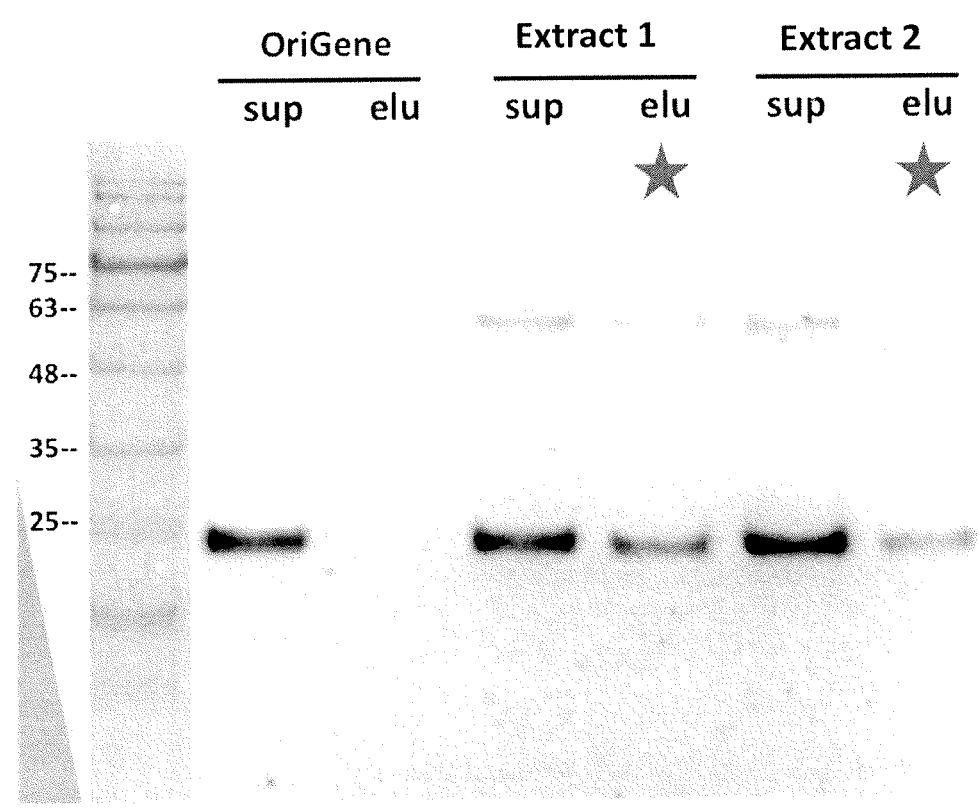
FIG. 6 shows the result for ASAH2 purification.

The result for ASAH2 purification is shown in FIG. 6. FIG. 6 shows that ASAH2 was indeed purified (extract 1 and extract 2 are proteins obtained from different batches). The amino acid sequence of ASAH2 is shown as SEQ ID NO. 2.

Example 2: Enzyme Immobilization

Method 1

0.4454 g heat-activated silica gel was placed in 7 mL CHCl$_3$, and APTS was added therein by a weight of ⅕ weight of heat-activated silica gel to form a mixture. After stirring at room temperature for 24 hours, the mixture was filtered. The obtained solid was drained in vacuum at 50° C. After the solid was drained, 5% glutaraldehyde (phosphate Buffer, pH=8, 1×TBS) was added to the solid, and stirred for 21 hours to form a solution. The solid in the solution was filtered out and washed with water and a solid substance was obtained. NEU2 (¹⁄100-10000 wt %) was added to the solid substance and diluted with phosphate buffer, 1×TBS pH=8 to a volume of 2 mL, and reacted with the solid substance at room temperature for 24 hours. Finally, the solid substance was filtered out and washed with phosphate buffer (pH=8) and an enzyme immobilized product (ITRI-Siw-Nu-01) was obtained.

Method 2

3-glycidoxypropyltrimethoxysilane was added to heat-activated silica gel in toluene by a weight of ⅕ weight of heat-activated silica gel, refluxed for 20 hours, and then filtered. The obtained solid was washed with acetone and then drained in vacuum. NEU2 (¹⁄100-10000 wt %) was added to the solid and stirred in phosphate buffer for 2 hours and 15 minutes, and then the solid was filtered out. The solid was washed with deionized water and a buffer (pH 8) to obtain an enzyme immobilized product.

Method 3

1 g cellulose beads in 15 mL water were adjusted to about pH 11 by a NaOH solution, and then 1 g cyanogen bromide was added therein at room temperature. After about 30 minutes, the cellulose beads were washed in deionized water and a phosphate buffer (pH 8) in order. NEU2 in a phosphate buffer was added to the cellulose beads by a weight ratio of 1/600, and stirred overnight. After that, the cellulose beads were washed in a phosphate buffer (pH 8) to obtain an enzyme immobilized product.

Method 4

0.5 g cellulose beads in 1.5 mL water were refluxed in 10 mL toluene, and then cellulose beads were filtered out and washed with acetone and a phosphate buffer (pH 8). After that, the cellulose beads were added to 5% (w/v) glutaraldehyde (phosphate buffer, pH 8) and stirred at room temperature for 21 hours. Afterward, the cellulose beads were filtered out, and washed in a phosphate buffer (pH 8) to obtain glutaraldehyde-activated-cellulose beads. NEU2 in a phosphate buffer was added to the cellulose beads by a weight ratio of 2/1000, and stirred overnight. After that, the cellulose beads were washed in a phosphate buffer (pH 8) to obtain an enzyme immobilized product.

Method 5

Hypogel® 200NH$_2$ were added to 5% (w/v) glutaraldehyde (phosphate buffer, pH 8) and stirred at room temperature for 21 hours. Afterward, the solid substance was filtered out, and washed with a phosphate buffer (pH 8) to obtain glutaraldehyde-activated gel. NEU2 (1/10000 wt %) was diluted with a phosphate buffer (pH=8) to a volume of 15 mL, and mixed with 1.13 g of the glutaraldehyde-activated gel at room temperature for 20 hours. Finally, the solid was filtered out and washed in a phosphate buffer (pH=8) to obtain an enzyme immobilized product.

Method 6

1 g diethylaminoethyl cellulose (DEAE cellulose) was washed in water, suspended in an NaOH solution (1 M aqueous solution), stirred for 10 minutes, and then filtered out and washed in water. The obtained solid substance was suspended in 10 mL dioxane to form a suspension. 2 g cyanuric chloride and 10 mL toluene were added to the suspension and stirred for 30 minutes and then the solid therein was filtered out. The solid was washed with dioxane, water and acetone in order and dried under reduced pressure to form an activated solid support. After that, NEU2 1/10000 (wt %) was added to the activated solid support and stirred for 18 hours. Afterward, the activated solid support was filtered out and washed in water to obtain an enzyme immobilized product.

Method 7

0.5 g chitosan beads were added to 10 mL 0.5% glutaraldehyde, and stirred at room temperature for 1 hour, and then washed with water, continuously and thoroughly to form activated beads. After that, the activated beads were reacted with NEU2 1/3500 (wt %) at room temperature for 2 hours, filtered out and then washed with deionized water to obtain an enzyme immobilized product.

Method 8

1 g cellulose hollow fiber, as per the procedures in Method 4, was activated by APTS and glutaraldehyde, and then reacted with NEU2 1/10000 (wt %) in phosphate buffer (pH=8), stirred overnight, and washed with a phosphate buffer (pH=8) to obtain an enzyme immobilized product.

Method 9

1 g cellulose hollow fiber, as per the procedures in Method 3, was activated by cyanogen bromide, and then reacted with NEU2 in phosphate buffer (pH=8), stirred overnight, washed with a phosphate buffer (pH=8) to obtain an enzyme immobilized product.

Method 10

ECR-8204F epoxy-acrylate resin was washed in deionized water, reacted with ASAH2 1/10000 (wt %), adjusted to a volume of 2 mL with a 0.2 M sodium phosphate buffer, and then stirred for 24 hours. After that, epoxy-acrylate resin was filtered out and washed in deionized water and 2M phosphate buffer (pH=8) to obtain about 52 mg of enzyme immobilized product (ITRI-EC-AS-01).

Method 11

Iontosorb MT200 cellulose beads were washed in deionized water. Next, the cellulose beads were washed with 3:7 water/dioxane, 7:3 water/dioxane, 100% dioxane in order. After that, dioxane was added to the cellulose beads, and CDI was added therein by a weight of ⅓ weight of cellulose beads, and stirred for about 0.5-1 hour to form a solution. The dioxane in the solution was removed under reduced pressure, and then NEU 2 was immediately added therein and stirred for about 2 hours and 15 minutes. After the reaction, the cellulose beads in the solution were filtered out and were washed in a buffer (pH=6.5) to obtain a wet product about 0.2 g (ITRI-CD-01).

Method 12

0.5 μg NEU2 was added to 2% w/v alginate aqueous solution to form a mixture solution. Next, the mixture solution was dropped into a stirring 2% $CaCl_2$ (w/v) aqueous solution by a syringe needle. After that, the $CaCl_2$ aqueous solution was continuously stirred for 30 minutes, and then particles formed in the $CaCl_2$ aqueous solution were filtered out and washed in deionized water to obtain a wet product (ITRI-A-01).

Example 3

Efficacy of Immobilized-NEU2 Filled Device

NEU2 was immobilized by Method 2 in Example 2, and then the immobilized NEU2 was filled into a tube to form a biochemistry reactive device (immobilized-NEU2 filled device) shown in FIG. 1B.

(1) Determination of Apoptosis

Endothelial cells of blood vessel were co-cultured with electronegative low-density lipoprotein (electronegative LDL) L5 (25 μg/mL; 50 μg/mL) and L5 (1.25 μg) which was treated by the mobilized-NEU2 filled device for 2 hours (treatment temperature 37° C., pH 7.4) for 24 hours, respectively. After that, apoptosis of the endothelial cells was determined, and the results are shown in FIG. 7.

Figure 7:
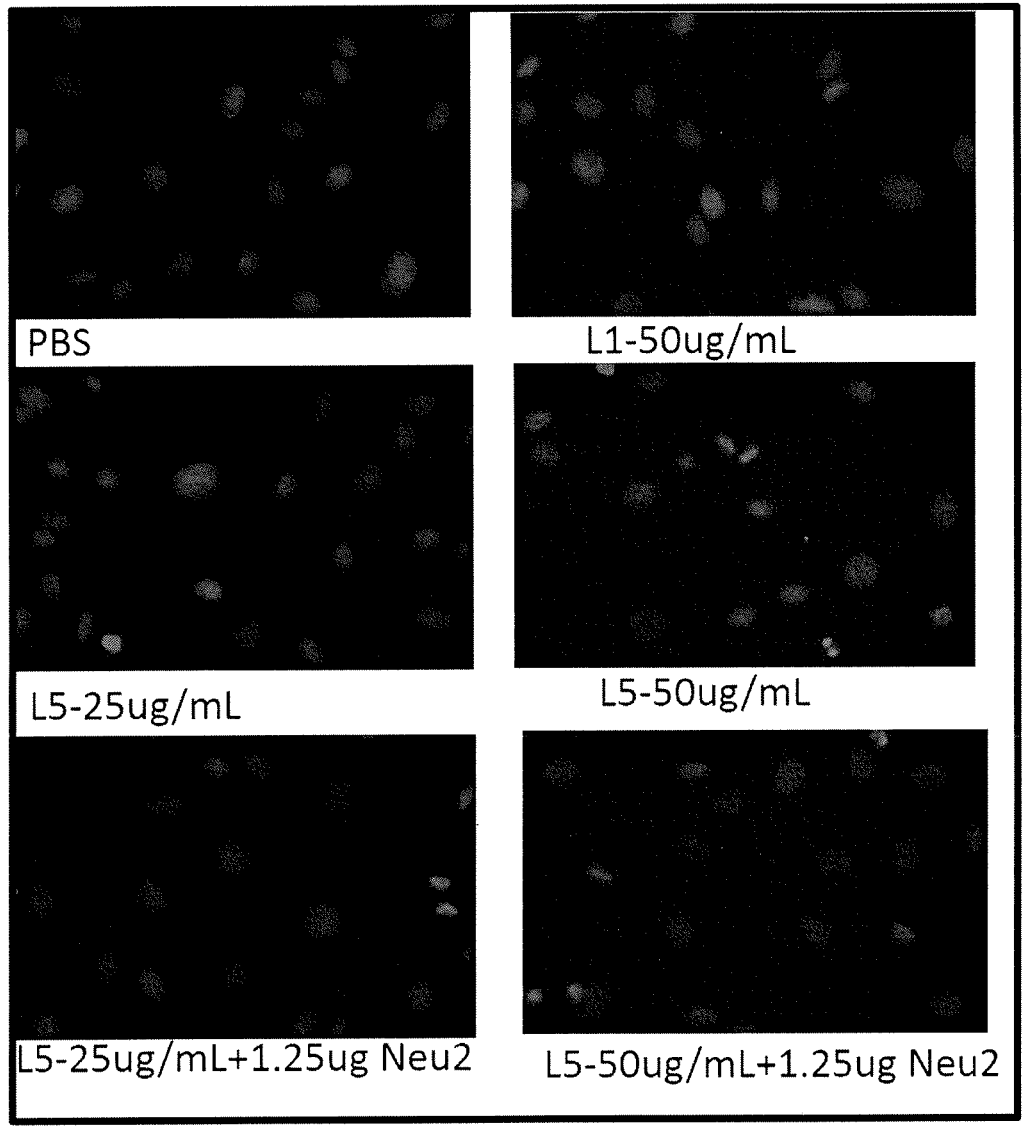
FIG. 7 shows apoptosis of endothelial cells of blood vessel co-cultured with electronegative low-density lipoprotein (electronegative LDL) L5 (25 µg/mL; 50 µg/mL) and L5 (1.25 µg) treated by the mrnobilized-NEU2 filled device for 2 hours (treatment temperature 37° C., pH 7.4) for 24 hours, respectively.

According to FIG. 7, it is known that 25 μg/mL L5 results in apoptosis to about 15% endothelial cells and 50 μg/mL L5 results in apoptosis to about 30% endothelial cells while after the treatment of 1.25 μg NEU2, apoptosis effect of L5 to endothelial cells is reduced.

(2) Quantitative Analysis for Electronegative Low-Density Lipoprotein (Electronegative LDL)

LDL samples were obtained from a heart disease patient. Quantitative analysis for L5 was performed on the LDL samples without treatment and those treated without enzyme at 37° C. for 2 hours or treated with NEU2 for 2 hours (treatment temperature 37° C. pH 7.4) to determine the content of L5 in the samples mentioned above. The results are shown in FIG. 8.

Figure 8:
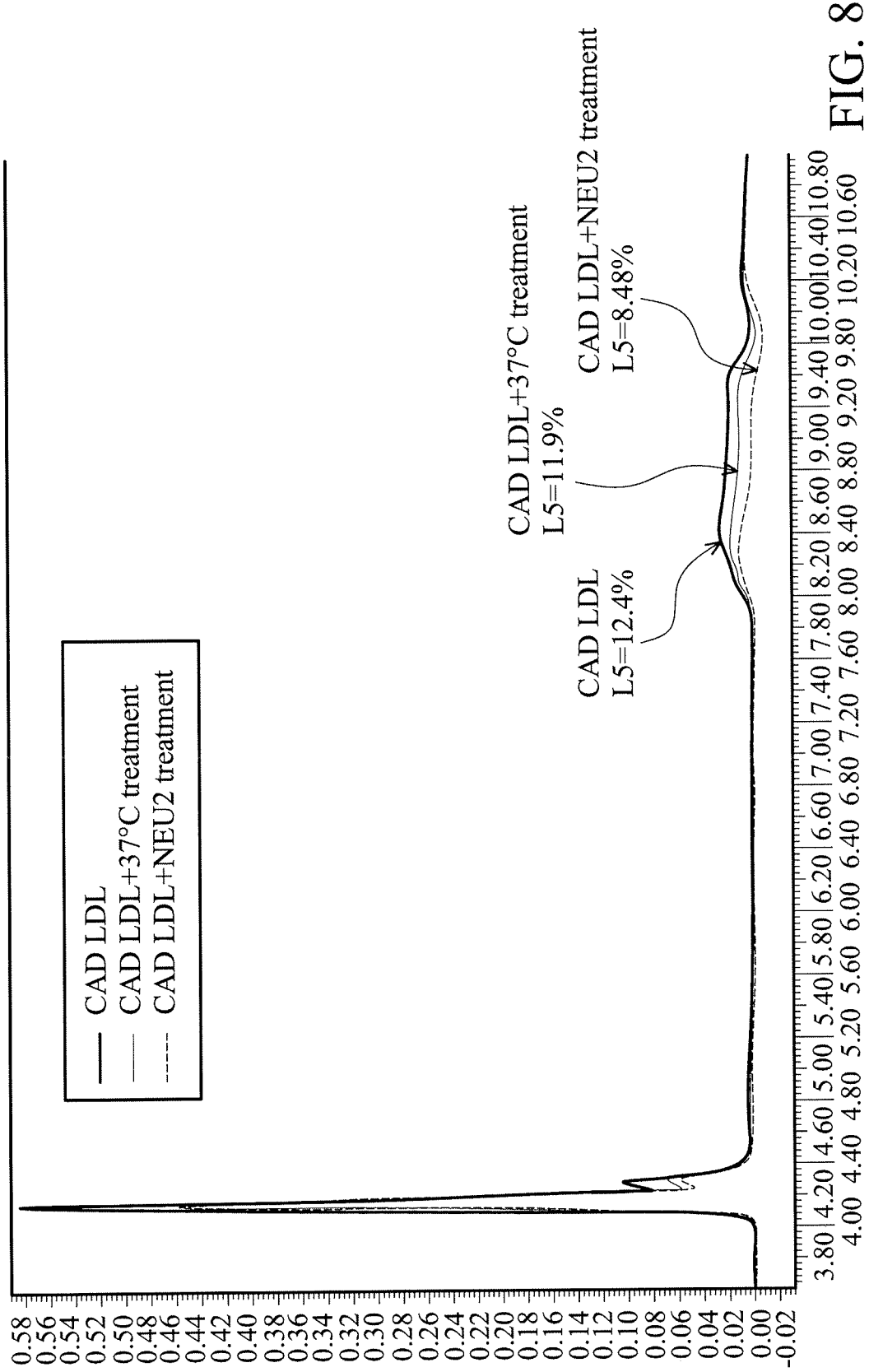
FIG. 8 shows results of performing quantitative analysis to the LDL samples without treatment and treated without enzyme at 37° C. for 2 hours or treated with NEU2 for 2 hours (treatment temperature 37° C. pH 7.4) to determine the content of L5 therein.

According to FIG. 8, it is known that after being treated with NEU2 enzyme for 2 hours, L5 content of the LDL sample was decreased from 12.4% to 8.48%.

(3) Mass Spectrometry

Mass spectrometry analysis was performed on L5 and L5 treated with NEU2 for 2 hours (treatment temperature 37° C., pH 7.4). The results are shown in FIGS. 9A, 9B and 9C.

It has been known that the feature of L5 is that serine and threonine of apolipoprotein E (apoE) are usually glycosylated.

Figure 9A:
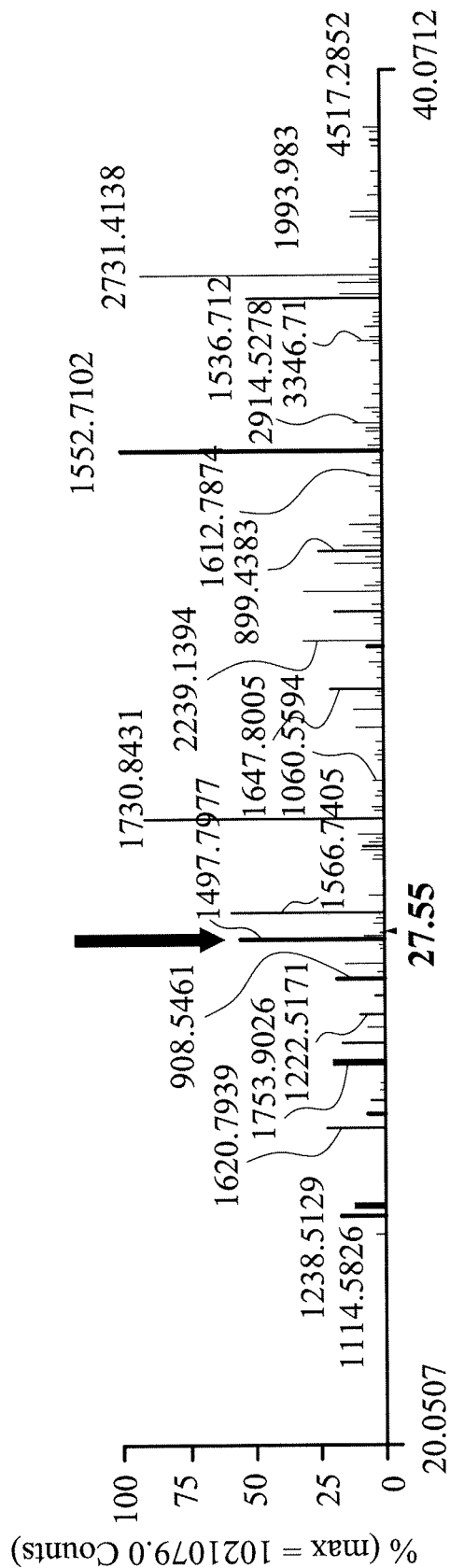
FIGS. 9A, 9B and 9C show that performing a mass spectrometry analysis on L5 can detect L5 specific glycosylation of apoE lipoprotein.
Figure 9B:
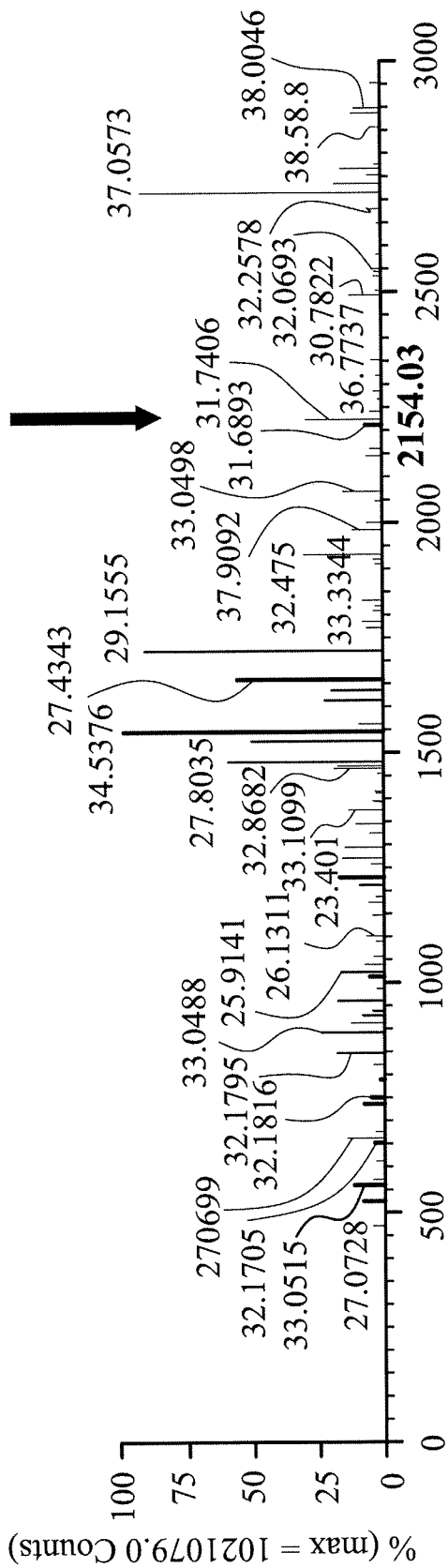
Figure 9C:
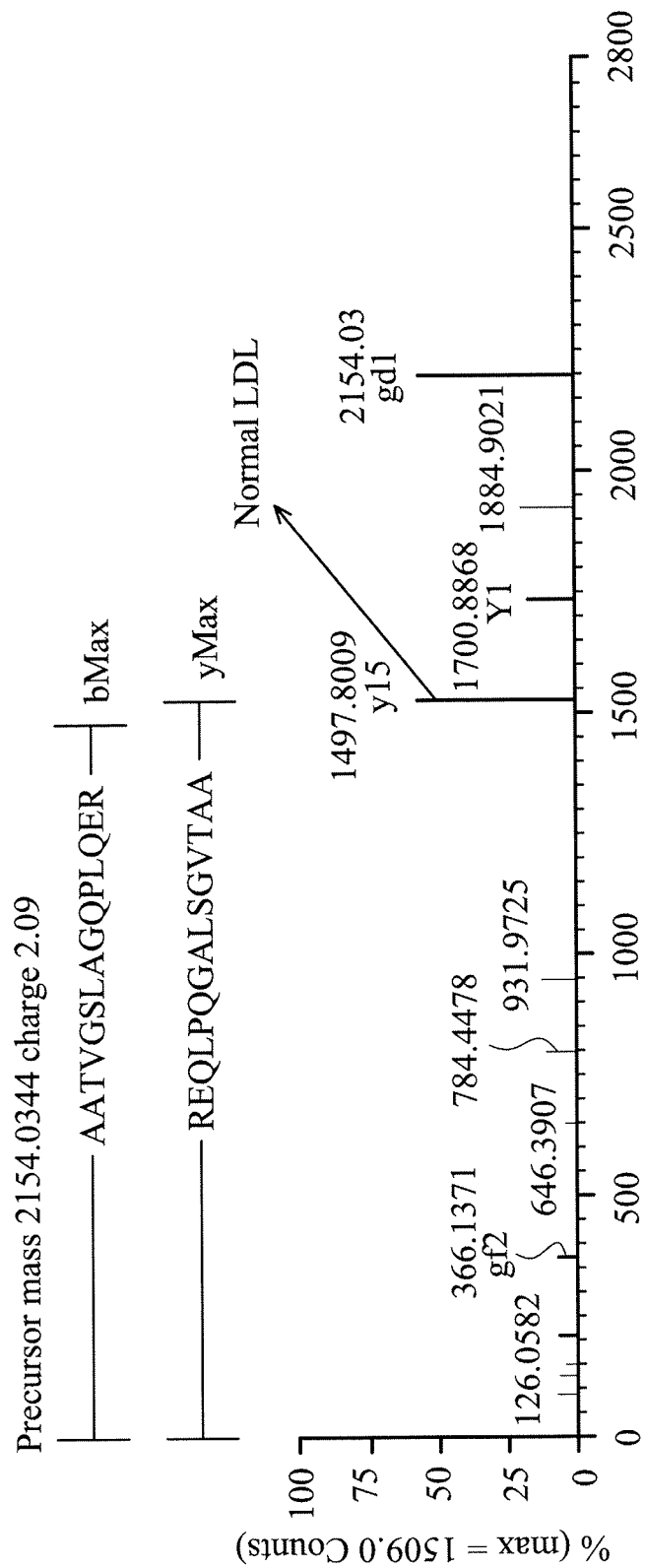

Refer to FIGS. 9A and 9B. Molecular weight 1497 indicates non-toxic LDL. Molecular weight of LDL with one glycosyl molecule is 1700, molecular weight of LDL with two glycosyl molecules is 1884, and molecular weight of LDL with three glycosyl molecules is 2154. FIG. 9C shows that the amino acid sequence of apolipoprotein E is glycosylated, and that results in the charge-to-mass ratio of the original peptide chain being increased from 1497.8009 to 1700.8868, 1884.9021 and 2154.0300.

FIGS. 10A1-2 show that there is no molecule with a charge-to-mass ratio of 1700, 1884 or 2154 that is detected for L5 treated by the immobilized-NEU2 filled device for 2 hours, and that indicates that there is no glycosylation on serine and threonine of apolipoprotein E, i.e., the glycan residues of LDL have been removed.

Figures 1, 10B:
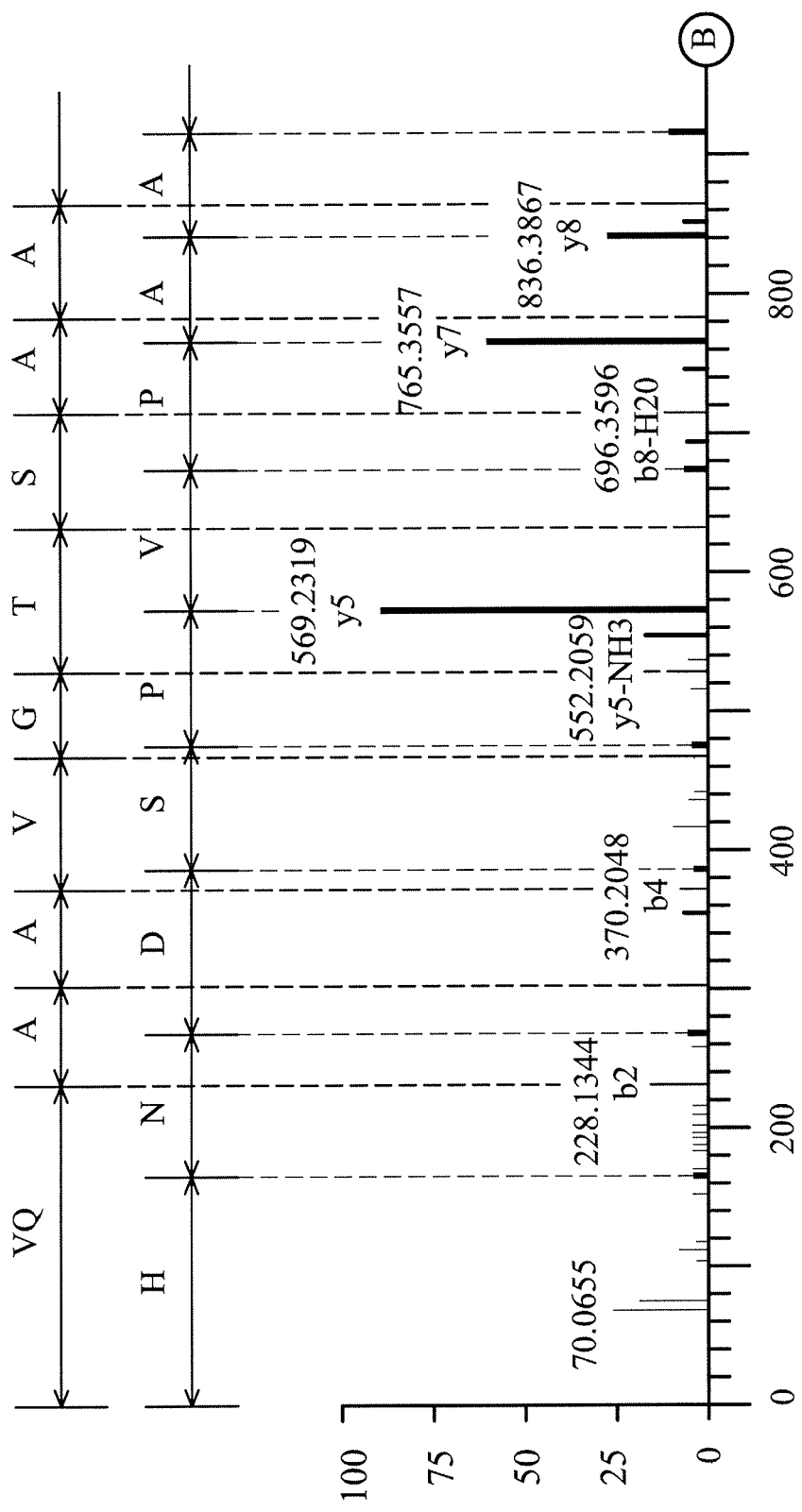
Figures 2, 10B:
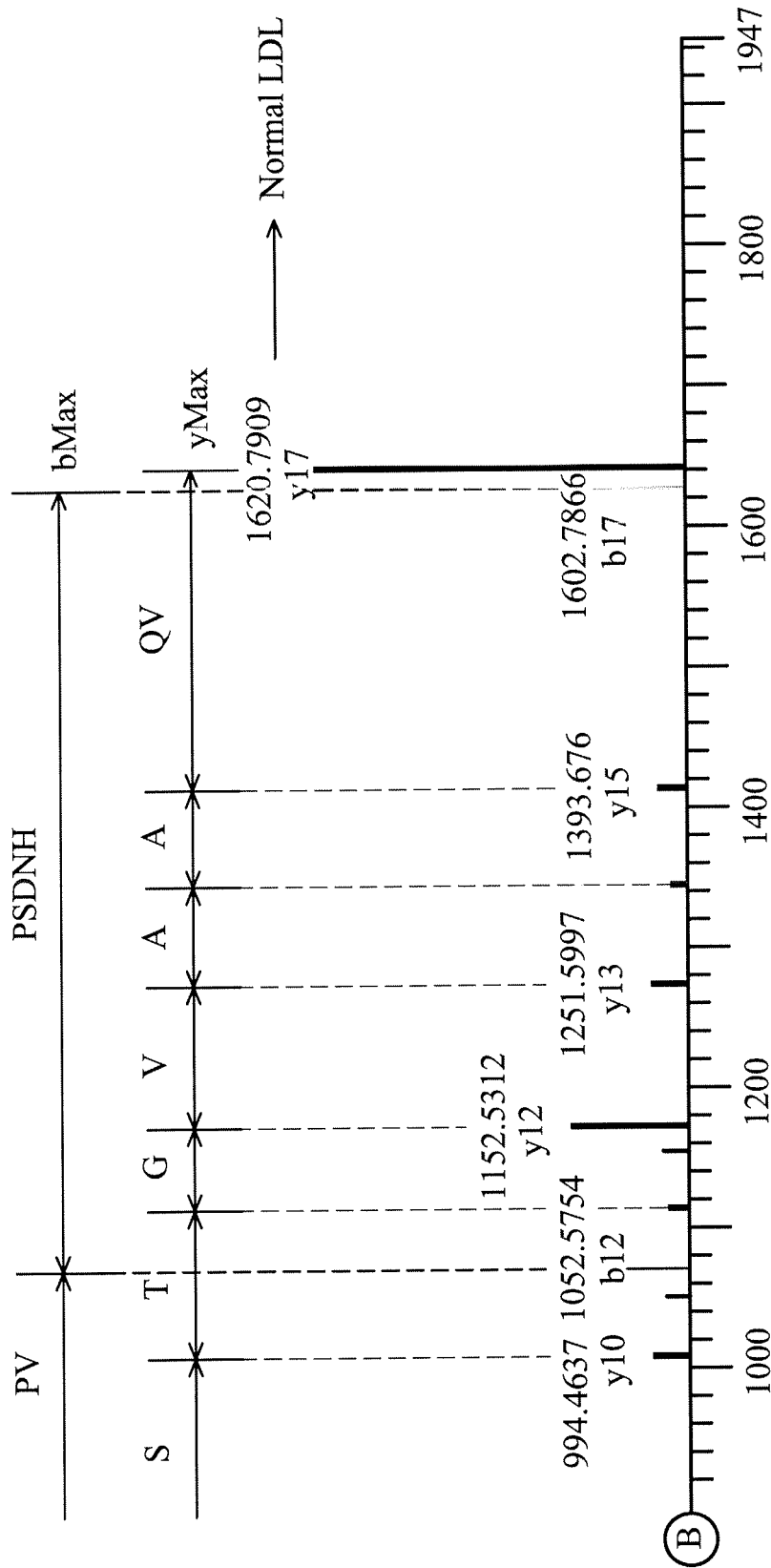
Figures 2, 11B:
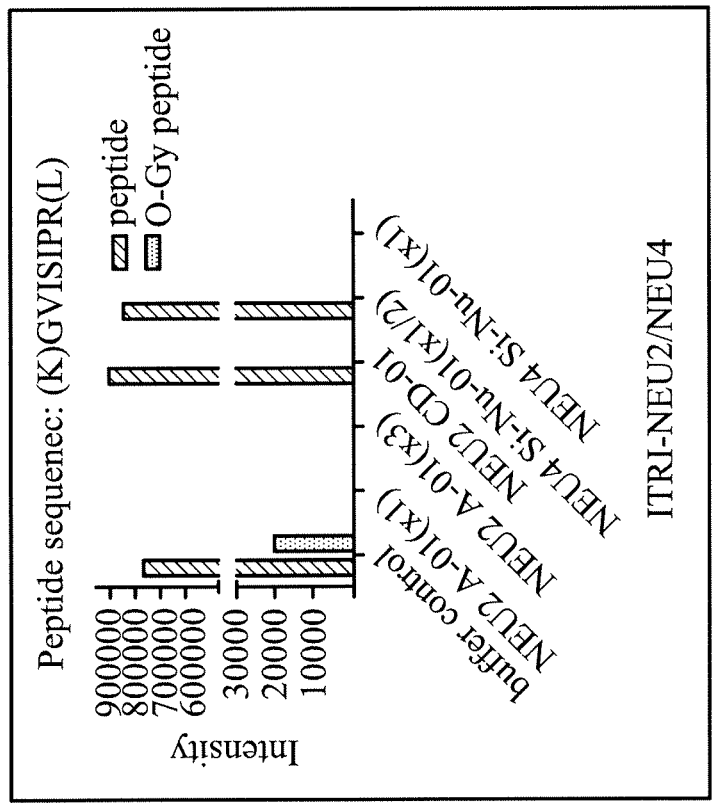
Figures 1, 11B:
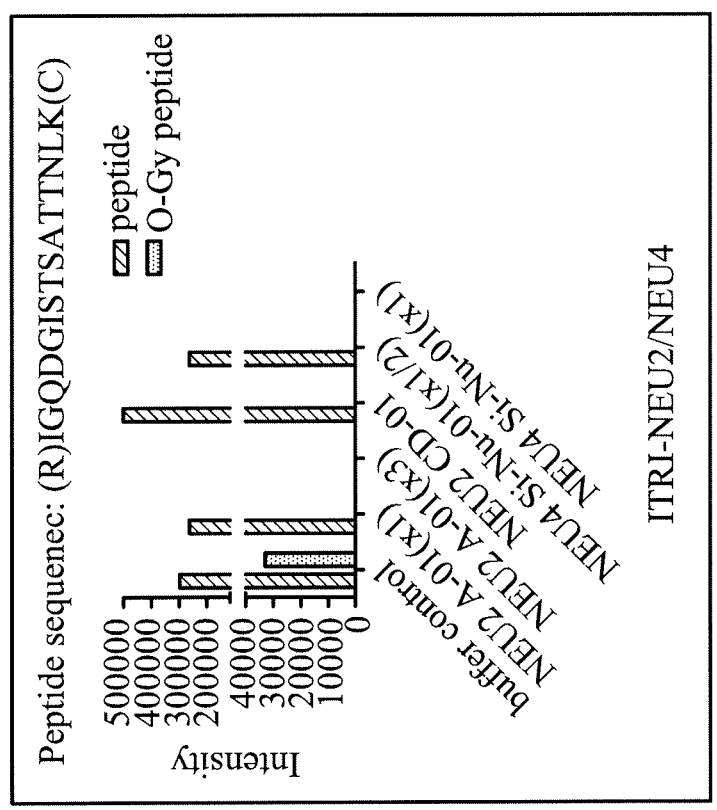
Figures 4, 11B:
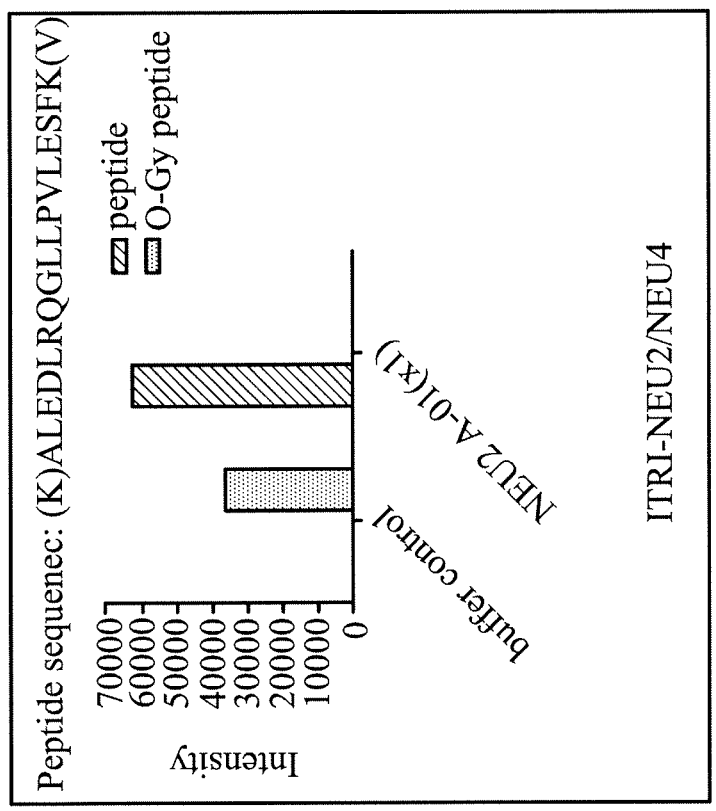
Figures 3, 11B:
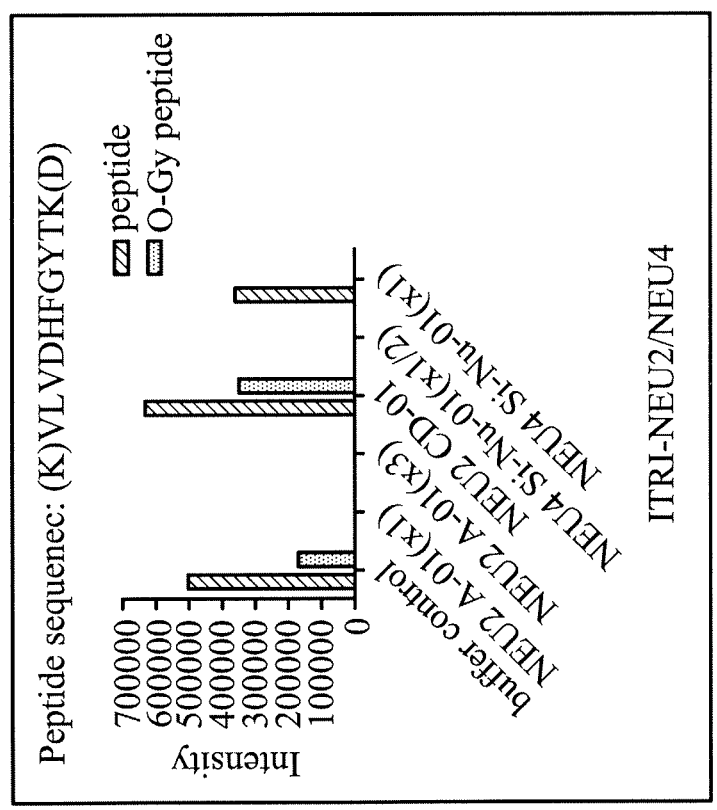

Similarly, FIGS. 10B1-2 show that for L5 treated by the immobilized-NEU2 filled device for 2 hours, there is no glycosylation on other sites of apolipoprotein E, and that indicates that the glycan residues of LDL have been removed.

Example 4

Efficacy of ASAH2

(1) LC/$MS^E$ Analysis for L5 Treated with ASAH2 for 24 Hours

L5 was treated with ASAH2 for 24 hours. LC/$MS^E$ analysis was performed on L5 without treatment and L5 with the preceding treatment to determine the ceramide content in the L5 samples mentioned above (for the detailed experimental methods, please see "5. Efficacy test for ASAH2" in "A. Method" of Example 1).

Figure 12:
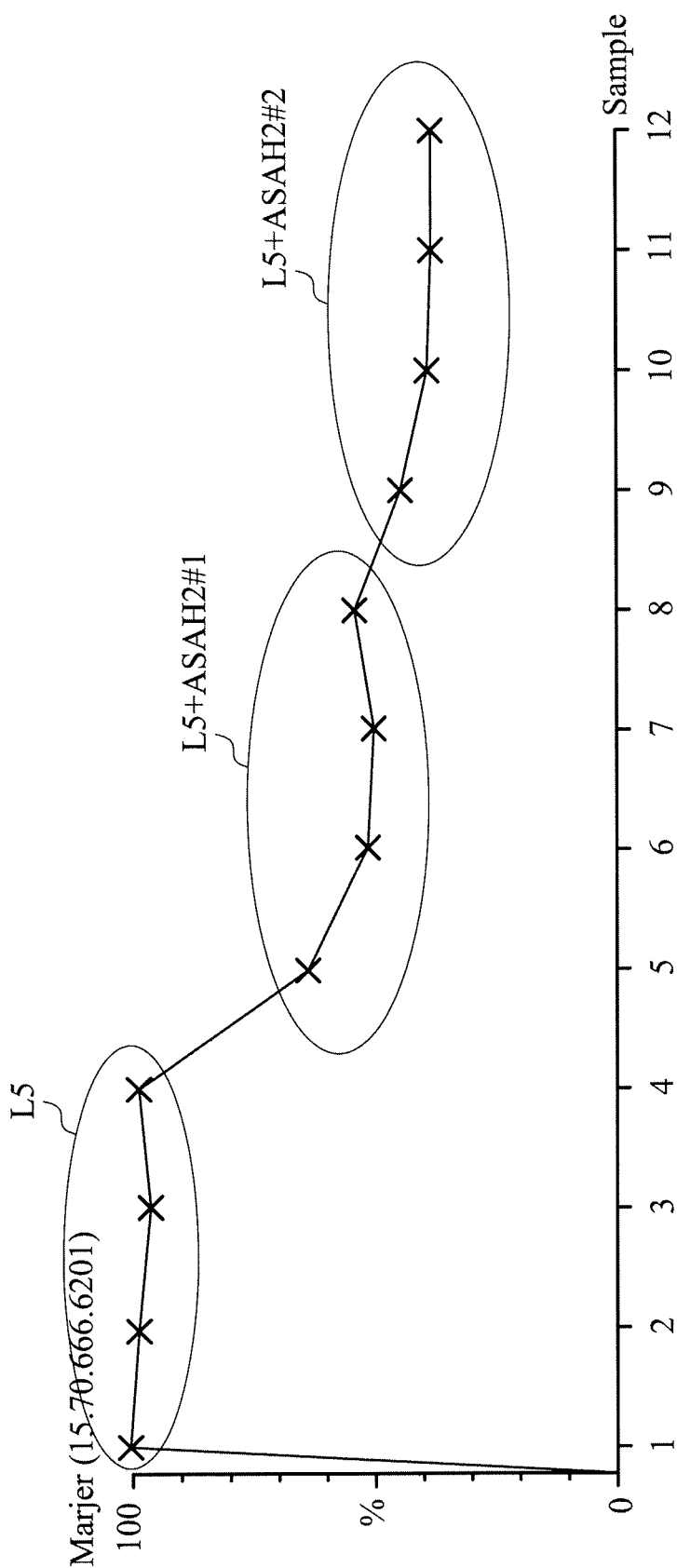
FIG. 12 shows ceramide contents of L5 and L5 treated with ASAH2 for 24 hours.

The results for LC/$MS^E$ analysis are shown in Table 1 (the four values shown in each group were obtained from determining the same sample four times). Conversion was performed to signal of each sample in Table 1 to obtain ceramide content percentage of each sample (the highest signal of the L5 without treatment was set as 100%), and the results are shown in FIG. 12. ASAH2 1 and ASAH2 2 shown in Table 1 and FIG. 12 are ASAH2 obtained from different batches.

TABLE 1

LC/$MS^E$ analysis results for L5 without treatment and L5 treated with ASAH2 for 24 hours

| | 24 hour baseline | ASAH2#1 treatment | ASAH2#2 treatment |
|---|---|---|---|
| Signal | 459.6464 | 295.3353 | 202.1154 |
| | 443.4776 | 236.9632 | 177.1598 |
| | 449.8201 | 230.7273 | 173.031 |
| | 451.5772 | 249.0337 | 175.7823 |

TABLE 1-continued

LC/MS$^E$ analysis results for L5 without treatment and L5 treated with ASAH2 for 24 hours

|  | 24 hour baseline | ASAH2#1 treatment | ASAH2#2 treatment |
|---|---|---|---|
| Mean | 451.1303 | 253.0149 | 182.0221 |
| Standard Deviation | 6.658431 | 29.21906 | 13.50503 |
| Decrease |  | 43.9 | 59.7 |

24-hour baseline represents ceramide content of L5 without treatment.

According to Table 1 and FIG. 12, it is known that after L5 was treated with ASAH2 for 24 hours, the ceramide content of L5 decreased significantly.

(2) LC/MS$^E$ Analysis for L5 Treated with ASAH2 for 24 Hours (for the Detailed Experimental Methods, Please See "5. Efficacy Test for ASAH2" in "A. Method" of Example 1)

L5 was treated with ASAH2 for 24 hours. LC/MS$^E$ analysis was performed on L5 without treatment and L5 with the preceding treatment to determine the ceramide content in the L5 samples mentioned above.

Figure 13:
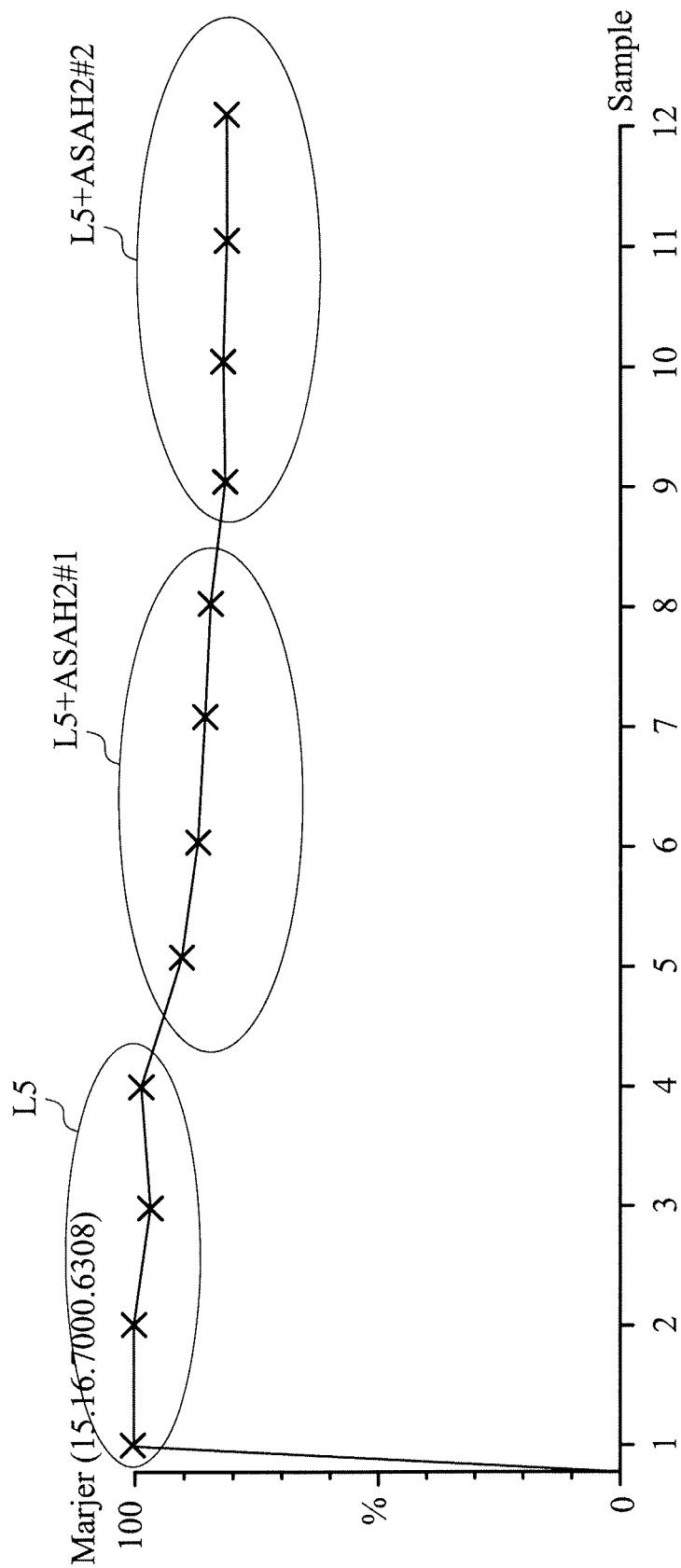
FIG. 13 shows ceramide contents of L5 and L5 treated with ASAH2 for 24 hours.

The results for LC/MS$^E$ analysis are shown in Table 2 (the four values shown in each group were obtained from determining the same sample four times). Conversion was performed to signal of each sample in Table 2 to obtain ceramide content percentage of each sample (the highest signal of the L5 without treatment was set as 100%), and the results are shown in FIG. 13. ASAH2 1 and ASAH2 2 shown in Table 2 and FIG. 13 are ASAH2 obtained from different batches.

TABLE 2

LC/MS$^E$ analysis results for L5 without treatment and L5 treated with ASAH2 for 24 hours

|  | 24 hour baseline | ASAH2#1 treatment | ASAH2#2 treatment |
|---|---|---|---|
| Signal | 2008.465 | 1827.823 | 1638.186 |
|  | 2007.321 | 1747.422 | 1627.067 |
|  | 1946.985 | 1725.032 | 1622.848 |
|  | 1989.728 | 1688.382 | 1616.651 |
| Mean | 1988.125 | 1747.165 | 1626.188 |
| Standard Deviation | 28.73594 | 59.02271 | 9.070668 |
| Decrease |  | 12.11997 | 18.20495 |

24 hour baseline represents ceramide content of L5 without treatment.

According to Table 2 and FIG. 13, it is known that after L5 was treated with ASAH2 for 24 hours, the ceramide content of L5 decreased significantly.

(3) LC/MS$^E$ Analysis for L5 Treated with ASAH2 in the Presence or Absence of a Buffer for 2 or 24 Hours In the presence or absence of a buffer (200 mM Tris-HCl pH 8.4, 1.5 M NaCl, 25 mM CaCl$_2$), L5 was treated with ASAH2 for 2 or 24 hours. LC/MS$^E$ analysis was performed on L5 without treatment and L5 with the preceding treatment to determine the ceramide content in the L5 samples mentioned above (for the detailed experimental methods, please see "5. Efficacy test for ASAH2" in "A. Method" of Example 1 except the part of mixing with the buffer or not).

Figure 14:
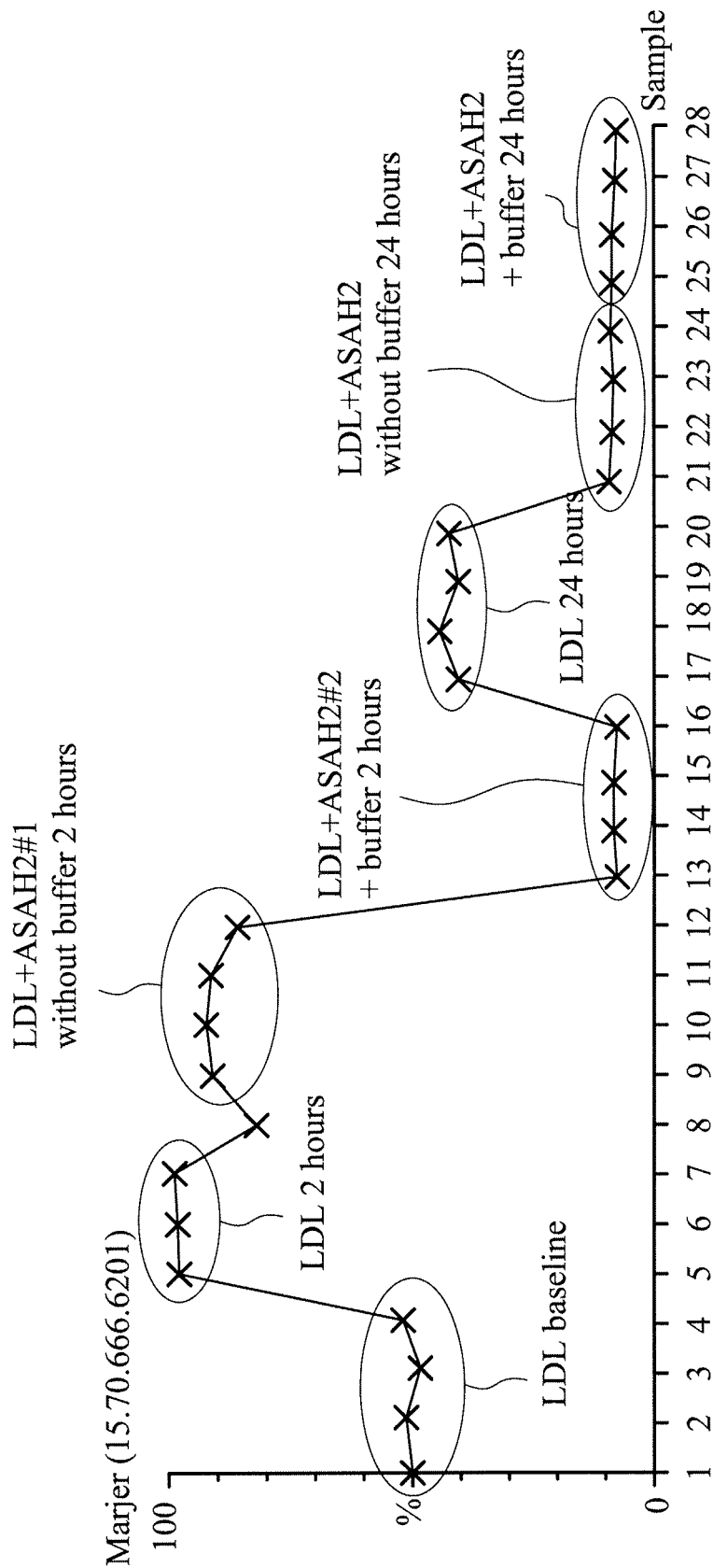
FIG. 14 shows ceramide contents of L5 and L5 treated with ASAH2 in the presence or absence of a buffer (200 mM Tris-HCl pH 8.4, 1.5 M NaCl, 25 mM CaCl$_2$) for 2 or 24 hours.

Conversion was performed to signal of each sample to obtain the ceramide content percentage of each sample (the highest signal of the L5 without treatment and kept for 2 hours was set as 100%), and the results are shown in FIG. 14. ASAH2 1 and ASAH2 2 shown in FIG. 14 are ASAH2 obtained from different batches. In FIG. 14, LDL baseline represents ceramide content of L5 without treatment and kept for 0 hour; LDL 2 hours represents ceramide content of L5 without treatment and kept for 2 hour; LDL 24 hours represents ceramide content of L5 without treatment and kept for 24 hour.

According to FIG. 14, it is known that, in the presence of a buffer, after L5 was treated with ASAH2 for 2 hours, the ceramide content of L5 decreased significantly. Moreover, in the presence or absence of a buffer, after L5 was treated with ASAH2 for 24 hours, the ceramide content of L5 both decreased significantly.

(4) LC/MS$^E$ Analysis for L5 Treated with ASAH2 in the Presence or Absence of a Buffer for 24 Hours In the presence or absence of a buffer (200 mM Tris-HCl pH 8.4, 1.5 M NaCl, 25 mM CaCl$_2$), L5 was treated with ASAH2 for 24 hours. LC/MS$^E$ analysis was performed on L5 without treatment and L5 with the preceding treatment to determine the ceramide content in the L5 samples mentioned above (for the detailed experimental methods, please see "5. Efficacy test for ASAH2" in "A. Method" of Example 1 except the part of mixing with the buffer or not).

Figure 15:
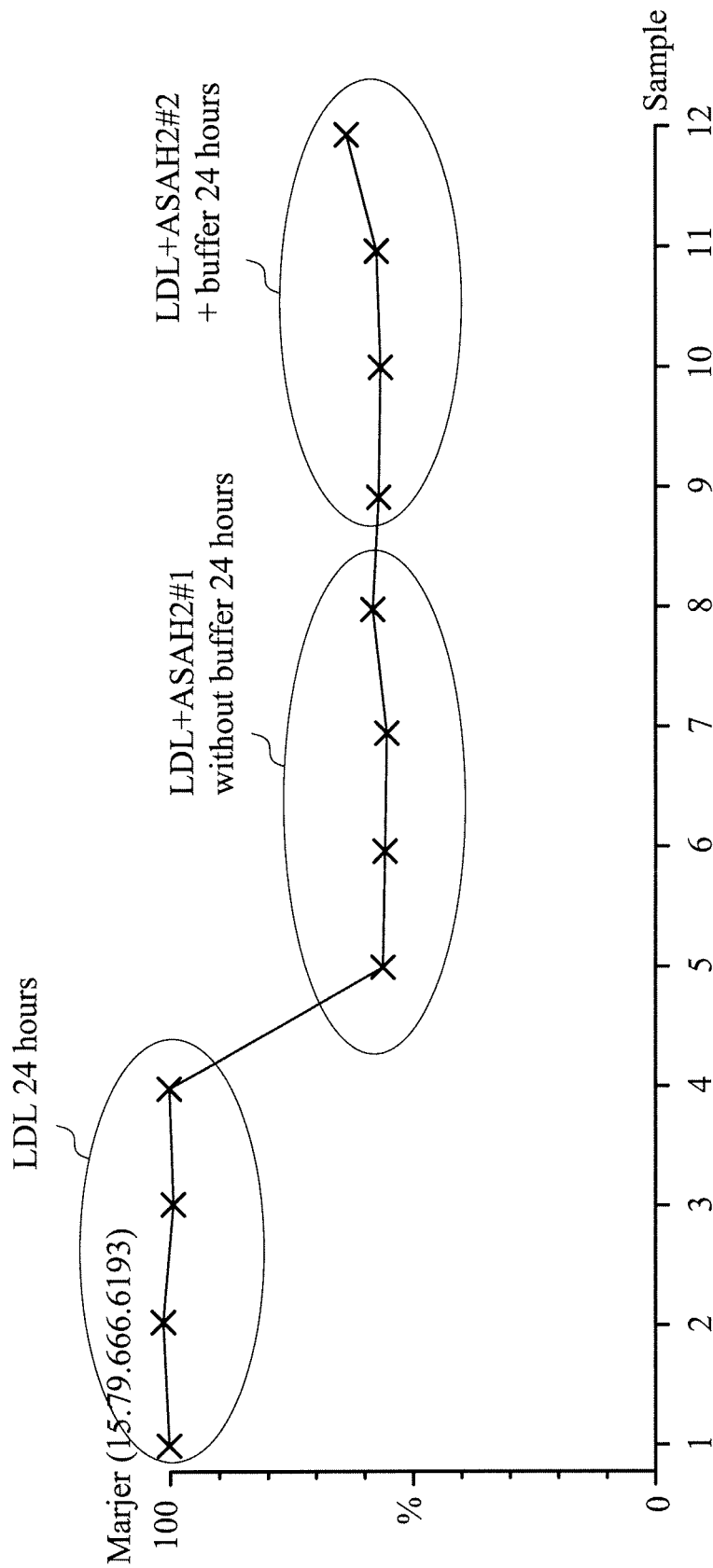
FIG. 15 shows ceramide contents of L5 and L5 treated with ASAH2 in the presence or absence of a buffer (200 mM Tris-HCl pH 8.4, 1.5 M NaCl, 25 mM CaCl$_2$) for 24 hours.

The results for LC/MS$^E$ analysis are shown in Table 3 (the four values shown in each group were obtained from determining the same sample four times). Conversion was performed to signal of each sample in Table 3 to obtain ceramide content percentage of each sample (the highest signal of the L5 without treatment was set as 100%), and the results are shown in FIG. 15. ASAH2 1 and ASAH2 2 shown in Table 3 and FIG. 15 are ASAH2 obtained from different batches.

TABLE 3

LC/MS$^E$ analysis results for L5 without treatment and L5 treated with ASAH2 in the presence or absence of a buffer for 24 hours

|  | 24 hour baseline | ASAH2#1 treatment | ASAH2#2 treatment |
|---|---|---|---|
| Signal | 217.36 | 122.40 | 121.87 |
|  | 220.16 | 122.08 | 121.65 |
|  | 214.80 | 117.11 | 123.68 |
|  | 215.96 | 121.81 | 136.51 |
| Mean | 217.07 | 120.85 | 125.93 |
| Standard Deviation | 2.31 | 2.51 | 7.11 |
| Decrease |  | 44.33 | 41.99 |

24 hour baseline represents ceramide content of L5 without treatment.

According to Table 3 and FIG. 15, it is known that in the presence or absence of a buffer, after L5 was treated with ASAH2 for 24 hours, the ceramide content of L5 both decreased significantly.

(5) LC/MS$^E$ Analysis for L5 Treated with ASAH2 for 24 Hours

Figure 16A:
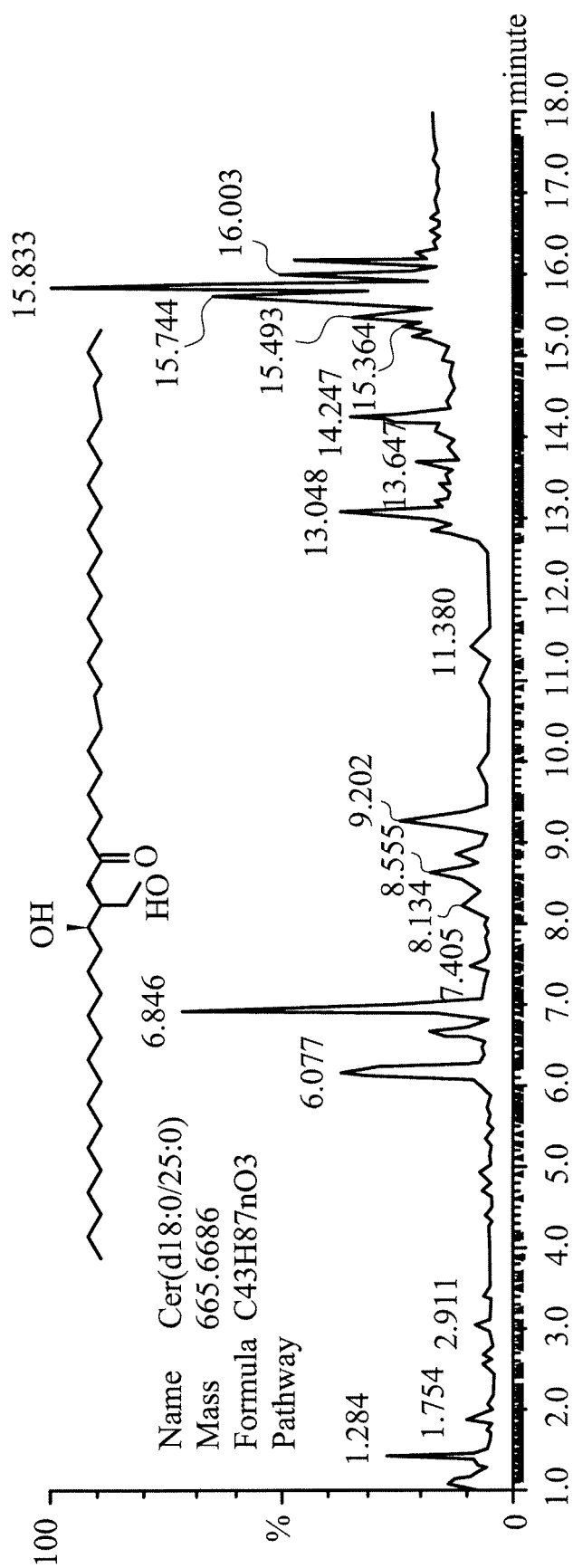
FIG. 16A shows the result of quantitative analysis for lipid constituents of L5 and L5 treated with ASAH2 for 24 hours mass spectrometry.

Quantitative analysis for lipid constituents was performed on L5 and L5 treated with ASAH2 for 24 hours by mass spectrometry, and the ceramide contents of the L5 samples mentioned above were compared. The results are shown in FIG. 16A.

Figure 16B:
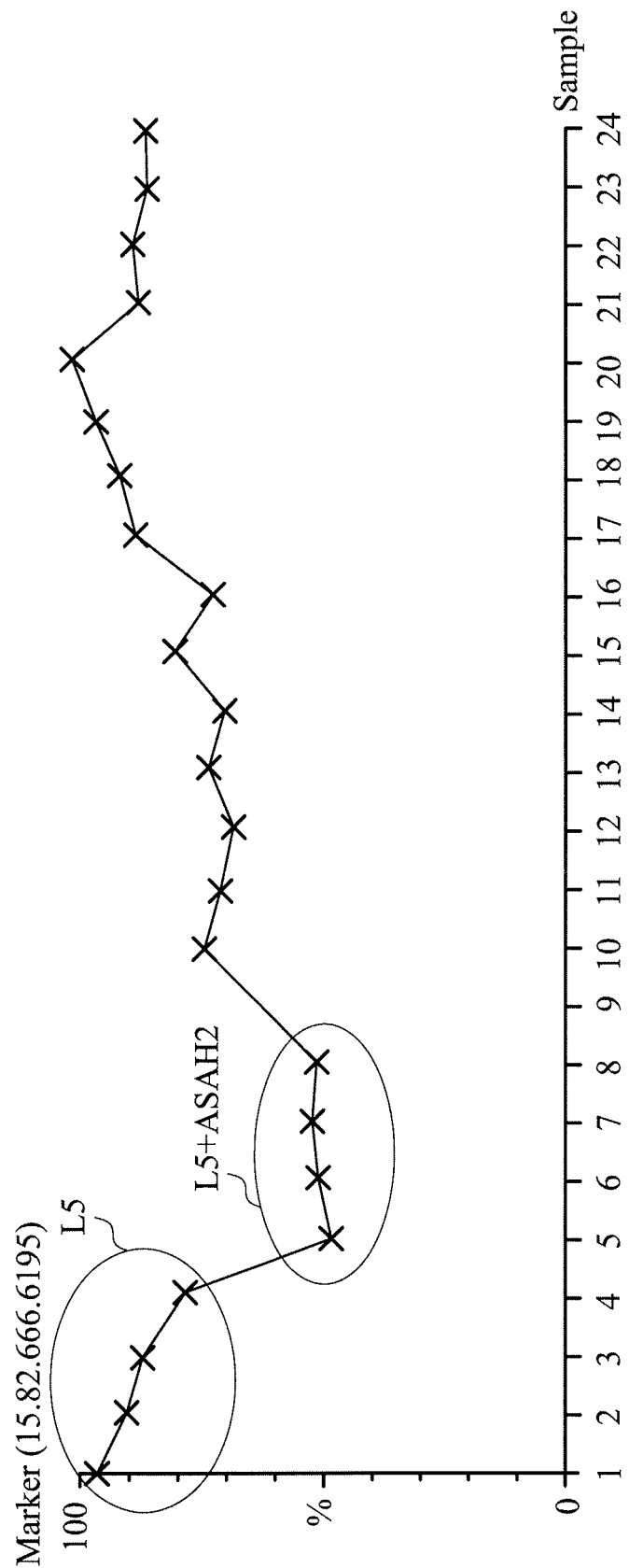
FIG. 16B shows ceramide contents of L5 and L5 treated with ASAH2 in the presence of a buffer (200 mM Tris-HCl pH 8.4, 1.5 M NaCl, 25 mM CaCl2)) for 2 hours.
Figure 17A:
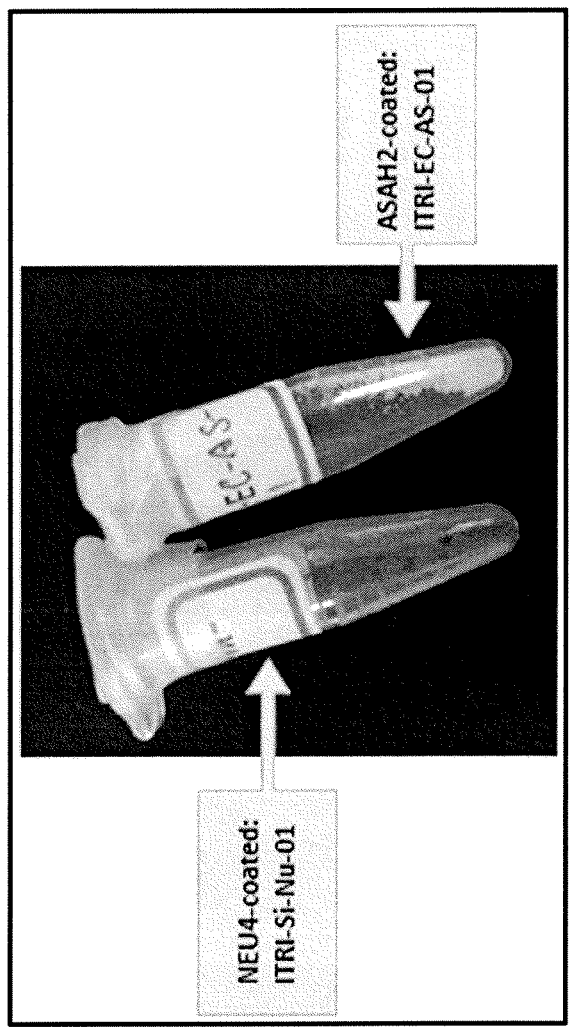
Figures 1, 17B:
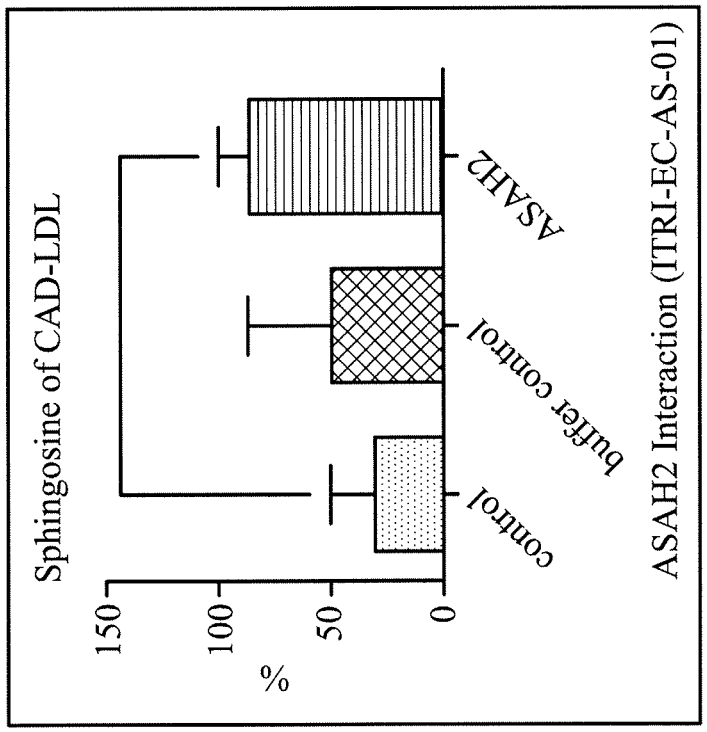
Figures 2, 17B:
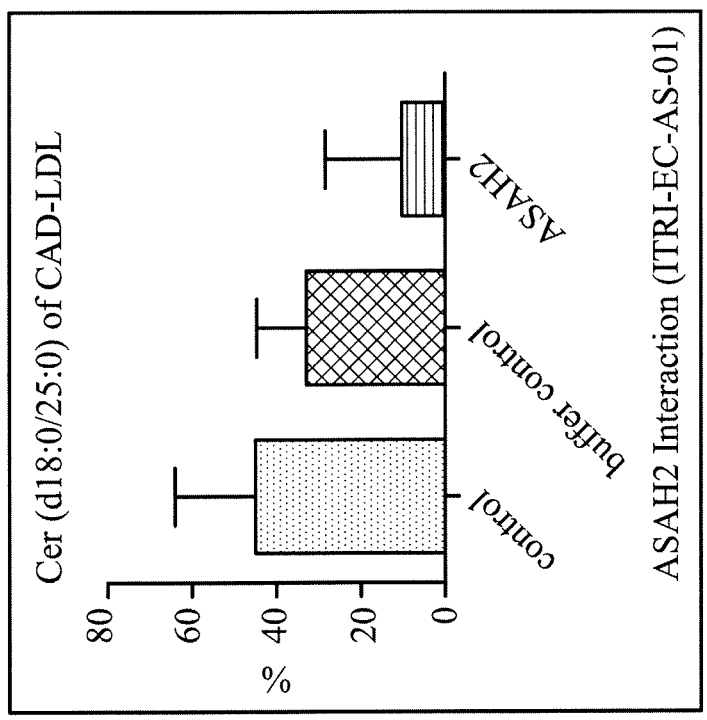

(6) LC/MS$^E$ Analysis for L5 Treated with ASAH2 in the Presence of a Buffer for 2 Hours In the presence of a buffer (200 mM Tris-HCl pH 8.4, 1.5 M NaCl, 25 mM CaCl$_2$), L5 was treated with ASAH2 for 2 hours. LC/MS$^E$ analysis was performed on L5 without treatment and L5 with the preceding treatment to determine the ceramide content in the L5 samples mentioned above (for the detailed experimental methods, please see "5. Efficacy test for ASAH2" in "A. Method" of Example 1 except the part of mixing with the buffer or not). The results for LC/MSE analysis are shown in Table 4 (the four values shown in each group were obtained from determining the same sample four times). Conversion was performed to signal of each sample in Table 4 to obtain ceramide content percentage of each sample (the highest signal of the L5 without treatment was set as 100%), and the results are shown in FIG. 16B.

TABLE 4

LC/MS$^E$ analysis results for L5 without treatment and L5 treated with ASAH2 in the presence or absence of a buffer for 2 hours

| Name of sample | Signal |
|---|---|
| L5 0 hour | 529.0532 |
| L5 0 hour | 498.5066 |
| L5 0 hour | 478.2745 |
| L5 0 hour | 432.8346 |

TABLE 4-continued

LC/MS$^E$ analysis results for L5 without treatment and L5 treated with ASAH2 in the presence or absence of a buffer for 2 hours

| Name of sample | Signal |
|---|---|
| L5 + ASAH 2 hours | 266.8874 |
| L5 + ASAH 2 hours | 276.2790 |
| L5 + ASAH 2 hour | 282.9767 |
| L5 + ASAH 2 hour | 283.6284 |

According to Table 4 and FIG. 16B, it is known that in the presence of a buffer, after L5 was treated with ASAH2 for 2 hours, the ceramide content of L5 decreased significantly.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A method for ex vivo treating blood or plasma, comprising:
   (a) ex vivo contacting a blood or plasma of a patient with acute myocardial infarction or heart disease patient with an enzyme composition to react the enzyme composition with the blood or plasma, wherein the enzyme composition is capable of eliminating electronegative low-density lipoprotein from the blood or plasma by the activity of the enzyme composition, and the enzyme composition is selected from a group consisting of:
   a first enzyme for eliminating a glycan residue of an electronegative low-density lipoprotein (LDL);
   a second enzyme for eliminating ceramide carried by a electronegative low-density lipoprotein (LDL); and
   a combination thereof; and
   (b) terminating contact between the blood or plasma and the enzyme composition to terminate the reaction of the enzyme composition with the blood or plasma.

2. The method for ex vivo treating blood or plasma as claimed in claim 1, wherein the step (a) is performed for about 0.25-8 hours.

3. The method for ex vivo treating blood or plasma as claimed in claim 1, wherein the step (a) is performed at about 4-40° C.

4. The method for ex vivo treating blood or plasma as claimed in claim 1, wherein the step (a) is performed at about pH 5-10.

5. The method for ex vivo treating blood or plasma as claimed in claim 1, wherein the first enzyme is sialidase or glycosidase.

6. The method for ex vivo treating blood or plasma as claimed in claim 5, wherein the sialidase is selected from a group consisting of:
   neuraminidase 1 (NEU1), neuraminidase 2 (NEU2), neuraminidase 3 (NEU3), neuraminidase 4 (NEU4) and O-sialidase bioengineered from human genome, one of the foregoing enzymes obtained through gene transformation, expression and purification, and sialidase from a virus or bacterium (alias, acetylneuraminyl hydrolase).

7. The method for ex vivo treating blood or plasma as claimed in claim 5, wherein the glycosidase is selected from a group consisting of:
   alpha- and beta-glucosidase bioengineered from human or animal genome, maltase-glucoamylase and sucrase-isomaltase, one of the foregoing enzymes obtained through gene transformation, expression and purification, and N-glycosidase F (PNGase F) and glucosidase from a virus or bacterium.

8. The method for ex vivo treating blood or plasma as claimed in claim 1, wherein the second enzyme is ceramidase.

9. The method for ex vivo treating blood or plasma as claimed in claim 8, wherein the ceramidase is selected from a group consisting of:
   N-acyl sphingosine amidohydrolase 1, N-acyl sphingosine amidohydrolase 2, N-acyl sphingosine amidohydrolase 2B, N-acyl sphingosine amidohydrolase 2C, N-acylethanolamine acid amidase, alkaline ceramidase 1, alkaline ceramidase 2 and alkaline ceramidase 3.

10. The method for ex vivo treating blood or plasma as claimed in claim 1, wherein the enzyme composition is the first enzyme.

11. The method for ex vivo treating blood or plasma as claimed in claim 10, wherein the first enzyme is neuraminidase 2.

12. The method for ex vivo treating blood or plasma as claimed in claim 1, wherein the enzyme composition is the second enzyme.

13. The method for ex vivo treating blood or plasma as claimed in claim 12, wherein the second enzyme is N-acylsphingosine amidohydrolase 2.

14. The method for ex vivo treating blood or plasma as claimed in claim 1, wherein the enzyme composition is the combination of the first enzyme and the second enzyme.

15. The method for ex vivo treating blood or plasma as claimed in claim 14, wherein the first enzyme is neuraminidase 2, and the second enzyme is N-acylsphingosine amidohydrolase 2.

16. The method for ex vivo treating blood or plasma as claimed in claim 1, wherein the enzyme composition is immobilized on a substrate.

17. The method for ex vivo treating blood or plasma as claimed in claim 16, the substrate comprises silica gel, cellulose, diethylaminoethyl cellulose, chitosan, polystyrene, polysulfone, polyethersulfone, resin or polysaccharide.

18. The method for ex vivo treating blood or plasma as claimed in claim 16, the substrate has a particle structure or a hollow-tube structure.

* * * * *

SEQUENCE LISTING

```
<160> NUMBER OF SEQ ID NOS: 7

<210> SEQ ID NO 1
<211> LENGTH: 380
<212> TYPE: PRT
<213> ORGANISM: Homo sapiens

<400> SEQUENCE: 1

Met Ala Ser Leu Pro Val Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Ile Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
```

```
                225                 230                 235                 240
Arg Ala Arg Val Gln Ala Gln Ser Thr Asn Asp Gly Leu Asp Phe Gln
                    245                 250                 255

Glu Ser Gln Leu Val Lys Lys Leu Val Glu Pro Pro Gln Gly Cys
                260                 265                 270

Gln Gly Ser Val Ile Ser Phe Pro Ser Pro Arg Ser Gly Pro Gly Ser
                275                 280                 285

Pro Ala Gln Trp Leu Leu Tyr Thr His Pro Thr His Ser Trp Gln Arg
            290                 295                 300

Ala Asp Leu Gly Ala Tyr Leu Asn Pro Arg Pro Ala Pro Glu Ala
305                 310                 315                 320

Trp Ser Glu Pro Val Leu Leu Ala Lys Gly Ser Cys Ala Tyr Ser Asp
                    325                 330                 335

Leu Gln Ser Met Gly Thr Gly Pro Asp Gly Ser Pro Leu Phe Gly Cys
                340                 345                 350

Leu Tyr Glu Ala Asn Asp Tyr Glu Glu Ile Val Phe Leu Met Phe Thr
                355                 360                 365

Leu Lys Gln Ala Phe Pro Ala Glu Tyr Leu Pro Gln
            370                 375                 380

<210> SEQ ID NO 2
<211> LENGTH: 780
<212> TYPE: PRT
<213> ORGANISM: Homo sapiens

<400> SEQUENCE: 2

Met Ala Lys Arg Thr Phe Ser Asn Leu Glu Thr Phe Leu Ile Phe Leu
1               5                   10                  15

Leu Val Met Met Ser Ala Ile Thr Val Ala Leu Leu Ser Leu Leu Phe
                20                  25                  30

Ile Thr Ser Gly Thr Ile Glu Asn His Lys Asp Leu Gly Gly His Phe
            35                  40                  45

Phe Ser Thr Thr Gln Ser Pro Pro Ala Thr Gln Gly Ser Thr Ala Ala
    50                  55                  60

Gln Arg Ser Thr Ala Thr Gln His Ser Thr Ala Thr Gln Ser Ser Thr
65                  70                  75                  80

Ala Thr Gln Thr Ser Pro Val Pro Leu Thr Pro Glu Ser Pro Leu Phe
                85                  90                  95

Gln Asn Phe Ser Gly Tyr His Ile Gly Val Gly Arg Ala Asp Cys Thr
                100                 105                 110

Gly Gln Val Ala Asp Ile Asn Leu Met Gly Tyr Gly Lys Ser Gly Gln
            115                 120                 125

Asn Ala Gln Gly Ile Leu Thr Arg Leu Tyr Ser Arg Ala Phe Ile Met
130                 135                 140

Ala Glu Pro Asp Gly Ser Asn Arg Thr Val Phe Val Ser Ile Asp Ile
145                 150                 155                 160

Gly Met Val Ser Gln Arg Leu Arg Leu Glu Val Leu Asn Arg Leu Gln
                165                 170                 175

Ser Lys Tyr Gly Ser Leu Tyr Arg Arg Asp Asn Val Ile Leu Ser Gly
            180                 185                 190

Thr His Thr His Ser Gly Pro Ala Gly Tyr Phe Gln Tyr Thr Val Phe
        195                 200                 205

Val Ile Ala Ser Glu Gly Phe Ser Asn Gln Thr Phe Gln His Met Val
    210                 215                 220
```

-continued

```
Thr Gly Ile Leu Lys Ser Ile Asp Ile Ala His Thr Asn Met Lys Pro
225                 230                 235                 240
Gly Lys Ile Phe Ile Asn Lys Gly Asn Val Asp Gly Val Gln Ile Asn
            245                 250                 255
Arg Ser Pro Tyr Ser Tyr Leu Gln Asn Pro Gln Ser Glu Arg Ala Arg
        260                 265                 270
Tyr Ser Ser Asn Thr Asp Lys Glu Met Ile Val Leu Lys Met Val Asp
    275                 280                 285
Leu Asn Gly Asp Asp Leu Gly Leu Ile Ser Trp Phe Ala Ile His Pro
290                 295                 300
Val Ser Met Asn Ser Asn His Leu Val Asn Ser Asp Asn Val Gly
305                 310                 315                 320
Tyr Ala Ser Tyr Leu Leu Glu Gln Glu Lys Asn Lys Gly Tyr Leu Pro
            325                 330                 335
Gly Gln Gly Pro Phe Val Ala Ala Phe Ala Ser Ser Asn Leu Gly Asp
        340                 345                 350
Val Ser Pro Asn Ile Leu Gly Pro Arg Cys Ile Asn Thr Gly Glu Ser
    355                 360                 365
Cys Asp Asn Ala Asn Ser Thr Cys Pro Ile Gly Gly Pro Ser Met Cys
370                 375                 380
Ile Ala Lys Gly Pro Gly Gln Asp Met Phe Asp Ser Thr Gln Ile Ile
385                 390                 395                 400
Gly Arg Ala Met Tyr Gln Arg Ala Lys Glu Leu Tyr Ala Ser Ala Ser
            405                 410                 415
Gln Glu Val Thr Gly Pro Leu Ala Ser Ala His Gln Trp Val Asp Met
        420                 425                 430
Thr Asp Val Thr Val Trp Leu Asn Ser Thr His Ala Ser Lys Thr Cys
    435                 440                 445
Lys Pro Ala Leu Gly Tyr Ser Phe Ala Ala Gly Thr Ile Asp Gly Val
450                 455                 460
Gly Gly Leu Asn Phe Thr Gln Gly Lys Thr Glu Gly Asp Pro Phe Trp
465                 470                 475                 480
Asp Thr Ile Arg Asp Gln Ile Leu Gly Lys Pro Ser Glu Glu Ile Lys
            485                 490                 495
Glu Cys His Lys Pro Lys Pro Ile Leu Leu His Thr Gly Glu Leu Ser
        500                 505                 510
Lys Pro His Pro Trp His Pro Asp Ile Val Asp Val Gln Ile Ile Thr
    515                 520                 525
Leu Gly Ser Leu Ala Ile Thr Ala Ile Pro Gly Glu Phe Thr Thr Met
530                 535                 540
Ser Gly Arg Arg Leu Arg Glu Ala Val Gln Ala Glu Phe Ala Ser His
545                 550                 555                 560
Gly Met Gln Asn Met Thr Val Val Ile Ser Gly Leu Cys Asn Val Tyr
            565                 570                 575
Thr His Tyr Ile Thr Thr Tyr Glu Glu Tyr Gln Ala Gln Arg Tyr Glu
        580                 585                 590
Ala Ala Ser Thr Ile Tyr Gly Pro His Thr Leu Ser Ala Tyr Ile Gln
    595                 600                 605
Leu Phe Arg Asn Leu Ala Lys Ala Ile Ala Thr Asp Thr Val Ala Asn
610                 615                 620
Leu Ser Arg Gly Pro Glu Pro Pro Phe Lys Gln Leu Ile Val Pro
625                 630                 635                 640
Leu Ile Pro Ser Ile Val Asp Arg Ala Pro Lys Gly Arg Thr Phe Gly
```

```
                        645                 650                 655
Asp Val Leu Gln Pro Ala Lys Pro Glu Tyr Arg Val Gly Glu Val Ala
                660                 665                 670

Glu Val Ile Phe Val Gly Ala Asn Pro Lys Asn Ser Val Gln Asn Gln
            675                 680                 685

Thr His Gln Thr Phe Leu Thr Val Glu Lys Tyr Glu Ala Thr Ser Thr
        690                 695                 700

Ser Trp Gln Ile Val Cys Asn Asp Ala Ser Trp Glu Thr Arg Phe Tyr
705                 710                 715                 720

Trp His Lys Gly Leu Leu Gly Leu Ser Asn Ala Thr Val Glu Trp His
                725                 730                 735

Ile Pro Asp Thr Ala Gln Pro Gly Ile Tyr Arg Ile Arg Tyr Phe Gly
                740                 745                 750

His Asn Arg Lys Gln Asp Ile Leu Lys Pro Ala Val Ile Leu Ser Phe
                755                 760                 765

Gly Gly Thr Ser Pro Ala Phe Glu Val Val Thr Ile
        770                 775                 780

<210> SEQ ID NO 3
<211> LENGTH: 17
<212> TYPE: PRT
<213> ORGANISM: Homo sapiens

<400> SEQUENCE: 3

Arg Ile Gly Gln Asp Gly Ile Ser Thr Ser Ala Thr Thr Asn Leu Lys
1               5                   10                  15

Cys

<210> SEQ ID NO 4
<211> LENGTH: 12
<212> TYPE: PRT
<213> ORGANISM: Homo sapiens

<400> SEQUENCE: 4

Lys Val Leu Val Asp His Phe Gly Tyr Thr Lys Asp
1               5                   10

<210> SEQ ID NO 5
<211> LENGTH: 9
<212> TYPE: PRT
<213> ORGANISM: Homo sapiens

<400> SEQUENCE: 5

Lys Gly Val Ile Ser Ile Pro Arg Leu
1               5

<210> SEQ ID NO 6
<211> LENGTH: 21
<212> TYPE: PRT
<213> ORGANISM: Homo sapiens

<400> SEQUENCE: 6

Lys Ser Gly Ser Ser Thr Ala Ser Trp Ile Gln Asn Val Asp Thr Lys
1               5                   10                  15

Tyr Gln Ile Arg Ile
            20

<210> SEQ ID NO 7
<211> LENGTH: 22
<212> TYPE: PRT
```

```
<213> ORGANISM: Homo sapiens

<400> SEQUENCE: 7

Lys Ala Lys Pro Ala Leu Glu Asp Leu Arg Gln Gly Leu Leu Pro Val
1               5                   10                  15

Leu Glu Ser Phe Lys Val
            20
```